United States Patent
Choudhary

(10) Patent No.: US 11,939,287 B2
(45) Date of Patent: Mar. 26, 2024

(54) RECOVERY OF MONOMERIC AND OLIGOMERIC BUILDING BLOCKS FROM POLYMERIC MATERIALS

(71) Applicant: Align Technology, Inc., San Jose, CA (US)

(72) Inventor: Umesh Upendra Choudhary, Santa Cruz, CA (US)

(73) Assignee: Align Technology, Inc., San Jose, CA (US)

(*) Notice: Subject to any disclaimer, the term of this patent is extended or adjusted under 35 U.S.C. 154(b) by 0 days.

(21) Appl. No.: 17/849,171

(22) Filed: Jun. 24, 2022

(65) Prior Publication Data
US 2023/0029131 A1 Jan. 26, 2023

Related U.S. Application Data

(60) Provisional application No. 63/214,717, filed on Jun. 24, 2021.

(51) Int. Cl.
| | | |
|---|---|---|
| *C07C 67/08* | (2006.01) | |
| *C07C 67/54* | (2006.01) | |
| *A61C 7/08* | (2006.01) | |

(52) U.S. Cl.
CPC .............. *C07C 67/08* (2013.01); *C07C 67/54* (2013.01); *A61C 7/08* (2013.01)

(58) Field of Classification Search
CPC . A61C 7/08; C07C 67/08; C07C 67/54; C08J 11/10; C08J 11/105; C08J 11/14; C08J 2300/10; C08J 2333/08; C08J 2333/10; Y02W 30/62; G03B 11/00; G03B 17/12; G03B 30/00; H01L 29/1054; H01L 29/158; H01L 29/42356; H01L 29/42392; H01L 29/66545; H01L 29/66613; H01L 29/66795; H01L 29/7846; H01L 29/785; H01L 29/78642; H04N 23/55; H04N 23/57
See application file for complete search history.

(56) References Cited

U.S. PATENT DOCUMENTS

| | | | |
|---|---|---|---|
| 5,820,368 A | 10/1998 | Wolk | |
| 5,975,893 A | 11/1999 | Chishti et al. | |
| 6,183,248 B1 | 2/2001 | Chishti et al. | |
| 6,309,215 B1 | 10/2001 | Phan et al. | |
| 6,386,864 B1 | 5/2002 | Kuo | |
| 6,450,807 B1 | 9/2002 | Chishti et al. | |
| 6,454,565 B2 | 9/2002 | Phan et al. | |
| 6,471,511 B1 | 10/2002 | Chishti et al. | |
| 6,524,101 B1 | 2/2003 | Phan et al. | |
| 6,572,372 B1 | 6/2003 | Phan et al. | |
| 6,607,382 B1 | 8/2003 | Kuo et al. | |
| 6,705,863 B2 | 3/2004 | Phan et al. | |
| 6,749,414 B1 | 6/2004 | Hanson et al. | |
| 6,783,604 B2 | 8/2004 | Tricca | |
| 6,790,035 B2 | 9/2004 | Tricca et al. | |
| 6,814,574 B2 | 11/2004 | Abolfathi et al. | |
| 6,830,450 B2 | 12/2004 | Knopp et al. | |
| 6,947,038 B1 | 9/2005 | Anh et al. | |
| 7,074,039 B2 | 7/2006 | Kopelman et al. | |
| 7,104,792 B2 | 9/2006 | Taub et al. | |
| 7,121,825 B2 | 10/2006 | Chishti et al. | |
| 7,160,107 B2 | 1/2007 | Kopelman et al. | |
| 7,192,273 B2 | 3/2007 | McSurdy, Jr. | |
| 7,347,688 B2 | 3/2008 | Kopelman et al. | |
| 7,354,270 B2 | 4/2008 | Abolfathi et al. | |
| 7,448,514 B2 | 11/2008 | Wen | |
| 7,481,121 B1 | 1/2009 | Cao | |
| 7,543,511 B2 | 6/2009 | Kimura et al. | |
| 7,553,157 B2 | 6/2009 | Abolfathi et al. | |
| 7,600,999 B2 | 10/2009 | Knopp | |
| 7,658,610 B2 | 2/2010 | Knopp | |
| 7,766,658 B2 | 8/2010 | Tricca et al. | |
| 7,771,195 B2 | 8/2010 | Knopp et al. | |
| 7,854,609 B2 | 12/2010 | Chen et al. | |
| 7,871,269 B2 | 1/2011 | Wu et al. | |
| 7,878,801 B2 | 2/2011 | Abolfathi et al. | |
| 7,878,805 B2 | 2/2011 | Moss et al. | |
| 7,883,334 B2 | 2/2011 | Li et al. | |
| 7,892,474 B2 | 2/2011 | Shkolnik et al. | |
| 7,914,283 B2 | 3/2011 | Kuo | |
| 7,947,508 B2 | 5/2011 | Tricca et al. | |
| 8,152,518 B2 | 4/2012 | Kuo | |
| 8,172,569 B2 | 5/2012 | Matty et al. | |
| 8,235,715 B2 | 8/2012 | Kuo | |
| 8,292,617 B2 | 10/2012 | Brandt et al. | |
| 8,337,199 B2 | 12/2012 | Wen | |

(Continued)

OTHER PUBLICATIONS

Das et al. (Activated Ester Containing Polymers: Opportunities and Challenges for the Design of Functional Macromolecules, Chemical Reviews, 116, pp. 1434-1495, Published 2015) (Year: 2015).*
He et al. (Postpolymerization Modification Using Less Cytotoxic Activated Ester Polymers for the Synthesis of Biological Active Polymers, Biomacromolecules, 15, pp. 3197-3205, Published 2014) (Year: 2014).*
Boudreaux et al. 1 (Controlled activity polymers. XI Hydrolytic release studies of hydrophilic copolymers with labile esters of model allelopathic phenols, J. of Controlled Release, 44, pp. 185-194, Published 1997) (Year: 1997).*
Boudreaux et al. 2 (Controlled activity polymers. X synthetically tailored monomers and copolymers with hydrolytically-labile esters of model allelopathic phenols, J. of Controlled Release, 44, pp. 185-194, Published 1997) (Year: 1997).*

(Continued)

*Primary Examiner* — Yevgeny Valenrod
*Assistant Examiner* — Blaine G Doletski
(74) *Attorney, Agent, or Firm* — Seed IP Law Group LLP

(57) ABSTRACT

The present disclosure provides methods and processes for the recovery of compounds (e.g., pendant groups) from polymeric materials, as well as methods for recycling and reusing such compounds by synthetically converting a recovered compound to building blocks that can be used in, e.g., curable resins for the fabrication of new devices, such as medical devices (e.g., orthodontic appliances).

27 Claims, 7 Drawing Sheets

(56) References Cited

U.S. PATENT DOCUMENTS

| | | |
|---|---|---|
| 8,401,686 B2 | 3/2013 | Moss et al. |
| 8,517,726 B2 | 8/2013 | Kakavand et al. |
| 8,562,337 B2 | 10/2013 | Kuo et al. |
| 8,641,414 B2 | 2/2014 | Borovinskih et al. |
| 8,684,729 B2 | 4/2014 | Wen |
| 8,708,697 B2 | 4/2014 | Li et al. |
| 8,758,009 B2 | 6/2014 | Chen et al. |
| 8,771,149 B2 | 7/2014 | Rahman et al. |
| 8,899,976 B2 | 12/2014 | Chen et al. |
| 8,899,977 B2 | 12/2014 | Cao et al. |
| 8,936,463 B2 | 1/2015 | Mason et al. |
| 8,936,464 B2 | 1/2015 | Kopelman |
| 9,022,781 B2 | 5/2015 | Kuo et al. |
| 9,119,691 B2 | 9/2015 | Namiranian et al. |
| 9,161,823 B2 | 10/2015 | Morton et al. |
| 9,241,774 B2 | 1/2016 | Li et al. |
| 9,326,831 B2 | 5/2016 | Cheang |
| 9,433,476 B2 | 9/2016 | Khardekar et al. |
| 9,610,141 B2 | 4/2017 | Kopelman et al. |
| 9,655,691 B2 | 5/2017 | Li et al. |
| 9,675,427 B2 | 6/2017 | Kopelman |
| 9,700,385 B2 | 7/2017 | Webber |
| 9,744,001 B2 | 8/2017 | Choi et al. |
| 9,844,424 B2 | 12/2017 | Wu et al. |
| 10,045,835 B2 | 8/2018 | Boronkay et al. |
| 10,111,730 B2 | 10/2018 | Webber et al. |
| 10,150,244 B2 | 12/2018 | Sato et al. |
| 10,201,409 B2 | 2/2019 | Mason et al. |
| 10,213,277 B2 | 2/2019 | Webber et al. |
| 10,299,894 B2 | 5/2019 | Tanugula et al. |
| 10,363,116 B2 | 7/2019 | Boronkay |
| 10,383,705 B2 | 8/2019 | Shanjani et al. |
| D865,180 S | 10/2019 | Bauer et al. |
| 10,449,016 B2 | 10/2019 | Kimura et al. |
| 10,463,452 B2 | 11/2019 | Matov et al. |
| 10,470,847 B2 | 11/2019 | Shanjani et al. |
| 10,492,888 B2 | 12/2019 | Chen et al. |
| 10,517,701 B2 | 12/2019 | Boronkay |
| 10,537,406 B2 | 1/2020 | Wu et al. |
| 10,537,463 B2 | 1/2020 | Kopelman |
| 10,548,700 B2 | 2/2020 | Fernie |
| 10,555,792 B2 | 2/2020 | Kopelman et al. |
| 10,588,776 B2 | 3/2020 | Cam et al. |
| 10,613,515 B2 | 4/2020 | Cramer et al. |
| 10,639,134 B2 | 5/2020 | Shanjani et al. |
| 10,743,964 B2 | 8/2020 | Wu et al. |
| 10,758,323 B2 | 9/2020 | Kopelman |
| 10,781,274 B2 | 9/2020 | Liska et al. |
| 10,813,720 B2 | 10/2020 | Grove et al. |
| 10,874,483 B2 | 12/2020 | Boronkay |
| 10,881,487 B2 | 1/2021 | Cam et al. |
| 10,912,629 B2 | 2/2021 | Tanugula et al. |
| 10,959,810 B2 | 3/2021 | Li et al. |
| 10,993,783 B2 | 5/2021 | Wu et al. |
| 11,026,768 B2 | 6/2021 | Moss et al. |
| 11,026,831 B2 | 6/2021 | Kuo |
| 11,045,282 B2 | 6/2021 | Kopelman et al. |
| 11,045,283 B2 | 6/2021 | Riley et al. |
| 11,103,330 B2 | 8/2021 | Webber et al. |
| 11,123,156 B2 | 9/2021 | Cam et al. |
| 11,154,382 B2 | 10/2021 | Kopelman et al. |
| 11,166,788 B2 | 11/2021 | Webber |
| 11,174,338 B2 | 11/2021 | Liska et al. |
| 11,219,506 B2 | 1/2022 | Shanjani et al. |
| 11,259,896 B2 | 3/2022 | Matov et al. |
| 11,273,011 B2 | 3/2022 | Shanjani et al. |
| 11,278,375 B2 | 3/2022 | Wang et al. |
| 11,318,667 B2 | 5/2022 | Mojdeh et al. |
| 11,331,166 B2 | 5/2022 | Morton et al. |
| 11,344,385 B2 | 5/2022 | Morton et al. |
| 11,376,101 B2 | 7/2022 | Sato et al. |
| 11,419,702 B2 | 8/2022 | Sato et al. |
| 11,419,710 B2 | 8/2022 | Mason et al. |
| 11,471,253 B2 | 10/2022 | Venkatasanthanam et al. |
| 11,497,586 B2 | 11/2022 | Kopelman |
| 11,504,214 B2 | 11/2022 | Wu et al. |
| 11,523,881 B2 | 12/2022 | Wang et al. |
| 11,534,268 B2 | 12/2022 | Li et al. |
| 11,534,974 B2 | 12/2022 | O'Leary et al. |
| 11,554,000 B2 | 1/2023 | Webber |
| 11,564,777 B2 | 1/2023 | Kopelman et al. |
| 11,571,278 B2 | 2/2023 | Kopelman et al. |
| 11,571,279 B2 | 2/2023 | Wang et al. |
| 11,576,750 B2 | 2/2023 | Kopelman et al. |
| 11,576,752 B2 | 2/2023 | Morton et al. |
| 11,589,955 B2 | 2/2023 | Medvinskaya et al. |
| 11,596,502 B2 | 3/2023 | Webber et al. |
| 11,602,414 B2 | 3/2023 | Sato et al. |
| 11,642,194 B2 | 5/2023 | Allen et al. |
| 11,642,198 B2 | 5/2023 | Avi et al. |
| 11,666,415 B2 | 6/2023 | Wang et al. |
| 2002/0192617 A1 | 12/2002 | Phan et al. |
| 2004/0166462 A1 | 8/2004 | Phan et al. |
| 2004/0166463 A1 | 8/2004 | Wen et al. |
| 2005/0014105 A1 | 1/2005 | Abolfathi et al. |
| 2005/0186524 A1 | 8/2005 | Abolfathi et al. |
| 2005/0244768 A1 | 11/2005 | Taub et al. |
| 2006/0019218 A1 | 1/2006 | Kuo |
| 2006/0078841 A1 | 4/2006 | Desimone et al. |
| 2006/0115782 A1 | 6/2006 | Li et al. |
| 2006/0115785 A1 | 6/2006 | Li et al. |
| 2006/0199142 A1 | 9/2006 | Liu et al. |
| 2006/0234179 A1 | 10/2006 | Wen et al. |
| 2008/0118882 A1 | 5/2008 | Su |
| 2008/0160473 A1 | 7/2008 | Li et al. |
| 2008/0286716 A1 | 11/2008 | Sherwood |
| 2008/0286717 A1 | 11/2008 | Sherwood |
| 2009/0280450 A1 | 11/2009 | Kuo |
| 2010/0055635 A1 | 3/2010 | Kakavand |
| 2010/0119646 A1* | 5/2010 | D'Orazio ............. A23K 50/75 426/531 |
| 2010/0129763 A1 | 5/2010 | Kuo |
| 2011/0269092 A1 | 11/2011 | Kuo et al. |
| 2014/0061974 A1 | 3/2014 | Tyler |
| 2014/0067334 A1 | 3/2014 | Kuo |
| 2014/0265034 A1 | 9/2014 | Dudley |
| 2015/0097316 A1 | 4/2015 | Desimone et al. |
| 2016/0193014 A1 | 7/2016 | Morton et al. |
| 2017/0007359 A1 | 1/2017 | Avi et al. |
| 2017/0015775 A1* | 1/2017 | Holmberg ............. C07C 69/54 |
| 2017/0135793 A1 | 5/2017 | Webber et al. |
| 2017/0156990 A1* | 6/2017 | Ruppert ............. A61F 2/30942 |
| 2018/0360567 A1 | 12/2018 | Xue et al. |
| 2019/0000592 A1 | 1/2019 | Cam et al. |
| 2019/0000593 A1 | 1/2019 | Cam et al. |
| 2019/0046297 A1 | 2/2019 | Kopelman et al. |
| 2019/0099129 A1 | 4/2019 | Kopelman et al. |
| 2019/0125497 A1 | 5/2019 | Mitra et al. |
| 2019/0144590 A1* | 5/2019 | Epps, III ............. C09J 133/08 429/308 |
| 2019/0262101 A1 | 8/2019 | Yaser et al. |
| 2019/0298494 A1 | 10/2019 | Webber et al. |
| 2020/0000553 A1 | 1/2020 | Svetlana et al. |
| 2020/0155276 A1 | 5/2020 | Cam et al. |
| 2020/0188062 A1 | 6/2020 | Avi et al. |
| 2020/0214598 A1 | 7/2020 | Huizhong et al. |
| 2021/0147672 A1 | 5/2021 | Cole et al. |

OTHER PUBLICATIONS

Enzyme Hydrolysis (pp. 1-5, Published 2019) (Year: 2019).*
Ester Hydrolysis (pp. 1-3, Published May 2021) (Year: 2021).*
Crommen et al., "Biodegradable polymers," *Biomaterials*, vol. 13, No. 9, Jan. 1, 1992, pp. 601-611 (11 pages).
Jenkins et al., "pendant group | side-group" definition on pp. 2297 of "Glossary of Basic Terms in Polymer Science," *Pure and Applied Chemistry*, vol. 68, No. 12, Dec. 1, 1996, pp. 2287-2311 (25 pages).

* cited by examiner

200 ⤴

┌─────────────────────────────────────┐
│ Determine a movement path to move   │
│ one or more teeth from an initial   │—210
│ arrangement to a target arrangement │
└─────────────────────────────────────┘
                  ↓
┌─────────────────────────────────────┐
│ Determine a force system to produce │
│ movement of the one or more teeth   │—220
│ along the movement path             │
└─────────────────────────────────────┘
                  ↓
┌─────────────────────────────────────┐
│ Determine an arch or palate expander│
│ design for an orthodontic appliance │—230
│ configured to produce the force system│
└─────────────────────────────────────┘
                  ↓
┌─────────────────────────────────────┐
│ Generate instructions for fabrication of │
│ the orthodontic appliance incorporating  │—240
│ the arch or palate expander design       │
└─────────────────────────────────────┘

FIG. 2

RECOVERY OF MONOMERIC AND OLIGOMERIC BUILDING BLOCKS FROM POLYMERIC MATERIALS

CROSS-REFERENCE TO RELATED APPLICATION

This application claims the priority of U.S. Provisional Patent Application No. 63/214,717, filed on Jun. 24, 2021, which is hereby incorporated by reference in its entirety.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND OF THE DISCLOSURE

The production of polymeric materials to fabricate devices such as medical devices can be cost and resource intensive. Thus, new approaches for reducing costs, energy and materials usage associated with the production of polymeric materials are desirable.

SUMMARY OF THE DISCLOSURE

The present disclosure provides methods and processes for the recovery of compounds (e.g., pendant groups) from polymeric material, as well as methods for recycling and reusing such compounds by synthetically converting a recovered compound to building blocks that can be used in, e.g., curable resins for the fabrication of devices, such as medical devices (e.g., orthodontic appliances).

In various aspects, the present disclosure provides a method of recovering a pendant group from a polymer, the method comprising: providing the polymer comprising the pendant group of Formula (I):

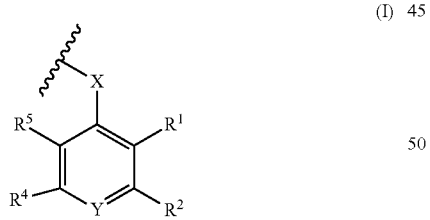

(I)

wherein, X is O, S or NH; Y is N or $CR^3$; and $R^1$, $R^2$, $R^3$, $R^4$, and $R^5$ are each independently H, substituted or unsubstituted $C_{1-6}$ alkyl, substituted or unsubstituted $C_{1-6}$ heteroalkyl, substituted or unsubstituted $C_{1-6}$ alkoxy, substituted or unsubstituted $C_{1-6}$ thioalkoxy, substituted or unsubstituted $C_{1-6}$ carbonyl, substituted or unsubstituted $C_{1-6}$ carboxyl, substituted or unsubstituted cyclo($C_{3-8}$) alkyl, substituted or unsubstituted cyclo($C_{3-8}$) heteroalkyl, or substituted or unsubstituted aryl, or substituted or unsubstituted heteroaryl, or $R^4$ and $R^5$ together form a 4-, 5-, 6-, 7-, or 8-membered ring selected from substituted or unsubstituted cyclo($C_{4-8}$) alkyl, substituted or unsubstituted cyclo($C_{4-8}$) heteroalkyl, substituted or unsubstituted aryl, or substituted or unsubstituted heteroaryl; hydrolyzing a bond coupling the pendant group to the backbone of the polymer to produce a mixture; and recovering the pendant group from the mixture.

In various aspects, the present disclosure provides a method of recovering a pendant group (e.g., one according to Formula (I)) from a polymer, the method comprising: providing the polymer comprising a synthetic polymer backbone; cleaving a bond coupling the pendant group to the synthetic polymer backbone to produce a mixture; and recovering the pendant group from the mixture. In some aspects, cleaving the bond comprises or consists of hydrolyzing the bond.

In some aspects, the hydrolyzing comprises base-mediated hydrolysis. In some aspect, the hydrolyzing comprises enzyme-mediated hydrolysis. In some aspects, the hydrolyzing comprises using a base at an elevated temperature. In some aspects, the elevated temperature is from 30° C. to 150° C. In some aspects, the base is an inorganic base. In some aspects, the inorganic base is an alkali metal hydroxide. In some aspects, the method further comprises distilling the mixture to produce a crude pendant group. In some aspects, the distilling comprises steam-distillation. In some aspects, the method further comprises purifying the crude pendant group using a chromatographic separation system to produce a fraction comprising the pendant group. In some aspects, the purified pendant group has a purity of at least about 70%, 80%, 90%, 95%, or 99% w/w based on dry solids. In some aspects, the fraction comprises at most 5% w/w impurities based on dry solids. In some aspects, the impurities comprise decomposition products. In some aspects, the method further comprises recovering at least 70%, 80%, 90%, or 95% of the pendant group relative to the amount of the pendant group present in the initial polymer. In some aspects, the pendant group is a compound according to Formula (II):

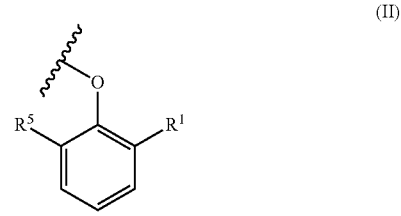

(II)

wherein $R^1$ and $R^5$ are each independently H, substituted or unsubstituted $C_{1-6}$ alkyl, substituted or unsubstituted $C_{1-6}$ heteroalkyl, substituted or unsubstituted $C_{1-6}$ alkoxy, substituted or unsubstituted $C_{1-6}$ thioalkoxy, substituted or unsubstituted $C_{1-6}$ carbonyl, substituted or unsubstituted $C_{1-6}$ carboxyl, substituted or unsubstituted cyclo($C_{3-8}$) alkyl, substituted or unsubstituted cyclo($C_{3-8}$) heteroalkyl, substituted or unsubstituted aryl, or substituted or unsubstituted heteroaryl, but not simultaneously H. In some aspects, the polymer comprises, in a polymerized form, a monomer comprising the pendant group, and wherein the monomer is a compound of Formula (X):

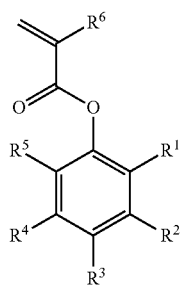

(X)

wherein $R^1$, $R^2$, $R^3$, $R^4$, and $R^5$ are each independently H, substituted or unsubstituted $C_{1-6}$ alkyl, substituted or unsubstituted $C_{1-6}$ heteroalkyl, substituted or unsubstituted $C_{1-6}$ alkoxy, substituted or unsubstituted $C_{1-6}$ thioalkoxy, substituted or unsubstituted $C_{1-6}$ carbonyl, substituted or unsubstituted $C_{1-6}$ carboxyl, substituted or unsubstituted cyclo-($C_{3-8}$) alkyl, substituted or unsubstituted cyclo($C_{3-8}$) heteroalkyl, substituted or unsubstituted aryl, or substituted or unsubstituted heteroaryl; and $R^6$ is H, halogen, or substituted or unsubstituted $C_{1-3}$ alkyl. In some aspects, the polymer comprises, in a polymerized form, a polyacrylate backbone. In some aspects, the polyacrylate backbone comprises, in a polymerized form, an acrylate moiety, a methacrylate moiety, or a combination thereof. In some aspects, the polymer is part of a polymeric material. In some aspects, the polymeric material is part of a device. In some aspects, the device is a medical device. In some aspects, the medical device is a dental appliance.

In various aspects, provided herein is a process comprising: providing a curable composition; curing the curable composition to generate a polymer comprising a pendant group; subjecting the polymer to reaction conditions to cleave a bond coupling the pendant group to the backbone of the polymer; and generating a mixture comprising the pendant group. In some aspects, the process further comprises distilling the mixture to produce a crude pendant group. In some aspects, the distilling comprises steam-distillation. In some aspects, the process further comprises purifying the crude pendant group using a chromatographic separation system to produce a fraction comprising the pendant group. In some aspects, the pendant group has a purity of at least 70%, 80%, 90%, or 95% w/w based on dry solids. In some aspects, the fraction comprises at most 5% w/w impurities based on dry solids. In some aspects, the impurities comprise decomposition products. In some aspects, the process further comprises recovering at least 70%, 80%, 90%, or 95% of the pendant group relative to the amount of the pendant group present in the polymer. In some aspects, the recovered pendant group is a compound according to Formula (IX):

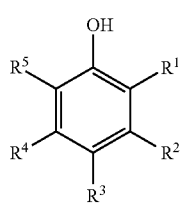

(IX)

wherein $R^1$, $R^2$, $R^3$, $R^4$, and $R^5$ are each independently H, substituted or unsubstituted $C_{1-6}$ alkyl, substituted or unsubstituted $C_{1-6}$ heteroalkyl, substituted or unsubstituted $C_{1-6}$ alkoxy, substituted or unsubstituted $C_{1-6}$ thioalkoxy, substituted or unsubstituted $C_{1-6}$ carbonyl, substituted or unsubstituted $C_{1-6}$ carboxyl, substituted or unsubstituted cyclo-($C_{3-8}$) alkyl, substituted or unsubstituted cyclo($C_{3-8}$) heteroalkyl, substituted or unsubstituted aryl, or substituted or unsubstituted heteroaryl. In some aspects, the process further comprises synthesizing a polymerizable monomer using the recovered pendant group. In some aspects, the polymerizable monomer is a compound according to Formula (X):

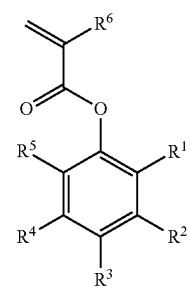

(X)

wherein $R^1$, $R^2$, $R^3$, $R^4$, and $R^5$ are each independently H, substituted or unsubstituted $C_{1-6}$ alkyl, substituted or unsubstituted $C_{1-6}$ heteroalkyl, substituted or unsubstituted $C_{1-6}$ alkoxy, substituted or unsubstituted $C_{1-6}$ thioalkoxy, substituted or unsubstituted $C_{1-6}$ carbonyl, substituted or unsubstituted $C_{1-6}$ carboxyl, substituted or unsubstituted cyclo-($C_{3-8}$) alkyl, substituted or unsubstituted cyclo($C_{3-8}$) heteroalkyl, substituted or unsubstituted aryl, or substituted or unsubstituted heteroaryl; and $R^6$ is H, halogen, or substituted or unsubstituted $C_{1-3}$ alkyl. In some aspect, $R^1$ and $R^5$ are methoxy, $R^2$, $R^3$, and $R^4$ are H, and $R^6$ is H or methoxy. In some aspects, the polymerizable monomer is used as a component of the curable composition. In some aspects, the bond coupling the pendant group to the backbone of the polymer is cleaved via hydrolysis. In some aspects, the hydrolysis comprises base-mediated hydrolysis. In some aspects, the hydrolysis comprises enzyme-mediated hydrolysis. In some aspects, the hydrolysis comprises using a base at an elevated temperature. In some aspects, the elevated temperature is from 30° C. to 150° C. In some aspects, the base is an inorganic base. In some aspects, the inorganic base is an alkali metal hydroxide. In some aspects, the polymer is part of a device. In some aspects, the device is a medical device. In some aspects, the medical device is a dental appliance. In some aspects, the dental appliance is a retainer, a palatal expander, or an aligner.

DESCRIPTION OF THE FIGURES

The novel features of the invention are set forth with particularity in the appended claims. A better understanding of the features and advantages of the present disclosure will be obtained by reference to the following detailed description that sets forth illustrative embodiments, in which the principles of the invention are utilized, and the accompanying drawings of which:

FIG. 2 illustrates a method for designing an orthodontic appliance, in accordance with embodiments.

DETAILED DESCRIPTION

Figure 1A:
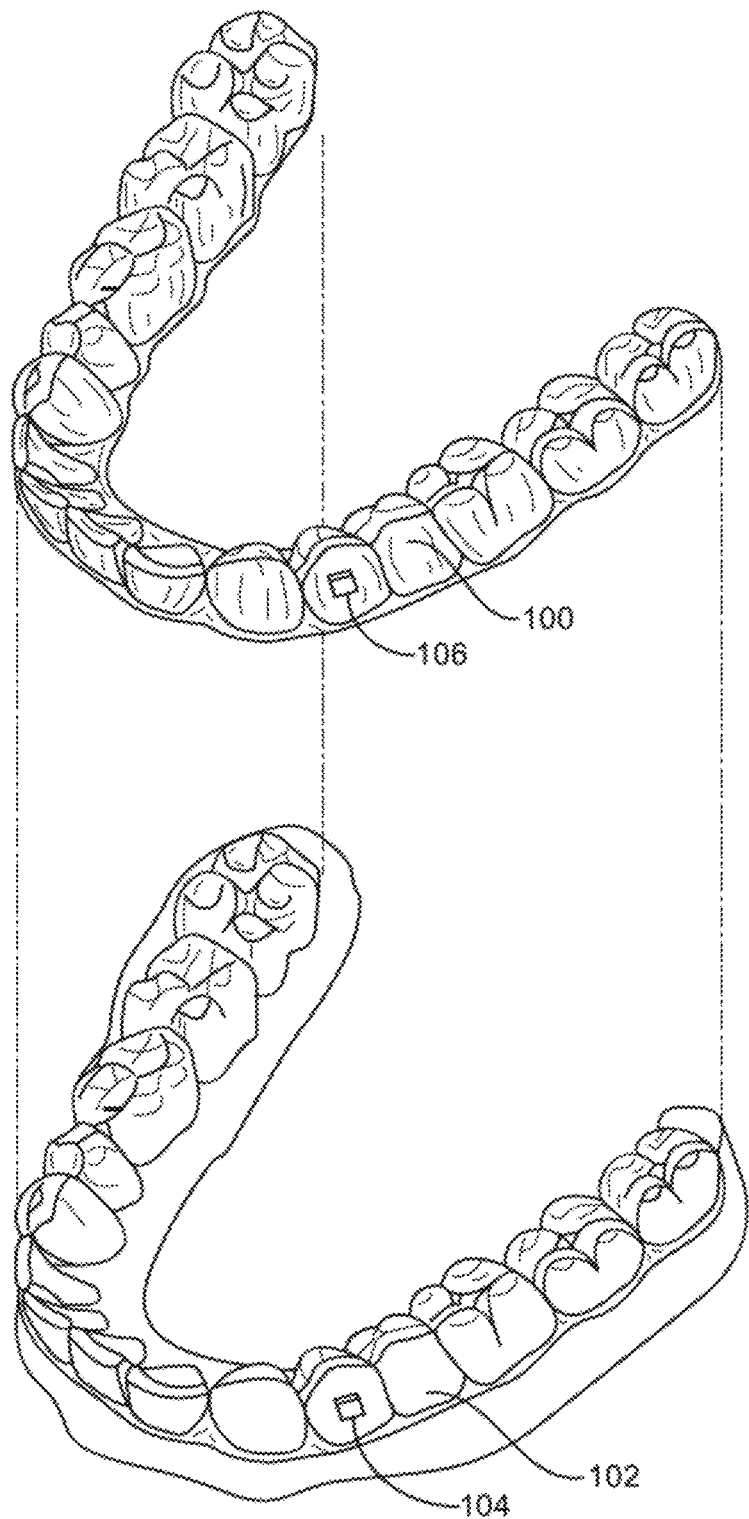
FIG. 1A illustrates a tooth repositioning appliance, in accordance with embodiments.

The present disclosure provides methods, processes, and compositions for recovering and recycling monomeric, oligomeric, and/or polymeric compounds from polymeric materials. The polymeric materials from which such components are recovered can be part of a device such as a medical device (e.g., an orthodontic appliance). Upon recovery and purification, the monomeric, oligomeric, and/or polymeric compounds of this disclosure can be synthetically converted into building blocks that can be reused in the fabrication of polymeric materials and hence significantly reduce the costs, resources, and energy requirements associated with the fabrication of such polymeric materials useful in various device applications (e.g., medical devices such as orthodontic appliances).

In various embodiments, a compound recovered from a polymeric material herein comprises or consists of a pendant group, i.e., a side groups coupled to an oligomeric or polymeric backbone. In such instances, provided herein are methods and processes for recovering and/or recycling a pendant group from a polymer, such method comprising cleaving a bond that couples the pendant group to the backbone of the polymer. Cleaving conditions can include a variety of different reagents, temperatures, pressures, etc., suitable for cleaving a bond coupling the pendant group to the polymer backbone. In some cases, such bond can be cleaved via hydrolysis, e.g., a base-mediated or enzyme-mediated hydrolysis.

Further provided herein are methods for reusing the recovered compounds, e.g., pendant groups, by, e.g., using such compounds to synthesize new building blocks or components for the fabrication of new materials, e.g., new polymeric materials.

As used herein, the term "pendant group" generally refers to a side group of an oligomer or polymer chain that is chemically bound (e.g., covalently bound) to the polymer backbone. Hence, a pendant group herein refers to a substituent coupled to a polymer backbone, but not the polymer backbone part itself. The following structure shows a portion of a polymeric backbone coupled to a pendant group according to embodiments of this disclosure:

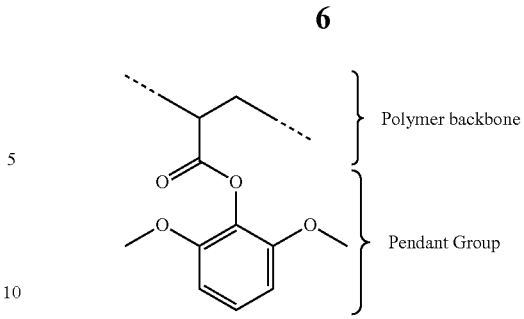

All terms, chemical names, expressions and designations have their usual meanings which are well-known to those skilled in the art. As used herein, the terms "to comprise" and "comprising" are to be understood as non-limiting, i.e., other components than those explicitly named may be included.

Number ranges are to be understood as inclusive, i.e. including the indicated lower and upper limits. Furthermore, the term "about", as used herein, and unless clearly indicated otherwise, generally refers to and encompasses plus or minus 10% of the indicated numerical value(s). For example, "about 10%" may indicate a range of 9% to 11%, and "about 1" may include the range 0.9-1.1.

As used herein, the term "polymer" generally refers to a molecule composed of repeating structural units connected by covalent chemical bonds and characterized by a substantial number of repeating units (e.g., equal to or greater than 20 repeating units and often equal to or greater than 100 repeating units and often equal to or greater than 200 repeating units) and a molecular weight greater than or equal to 5,000 Daltons (Da) or 5 kDa, such as greater than or equal to 10 kDa, 15 kDa, 20 kDa, 30 kDa, 40 kDa, 50 kDa, or 100 kDa. Polymers are commonly the polymerization product of one or more monomer precursors. The term polymer includes homopolymers, i.e., polymers consisting essentially of a single repeating monomer species. The term polymer also includes copolymers which are formed when two or more different types of monomers are linked in the same polymer. Copolymers may comprise two or more monomer subunits, and include random, block, alternating, segmented, grafted, tapered and other copolymers. The term "cross-linked polymers" generally refers to polymers having one or multiple links between at least two polymer chains, which can result from multivalent monomers forming cross-linking sites upon polymerization.

As used herein, the term "oligomer" generally refers to a molecule composed of repeating structural units connected by covalent chemical bonds and characterized by a number of repeating units less than that of a polymer (e.g., equal to or less than 10 repeating units) and a lower molecular weight than polymers (e.g., less than 5,000 Da or 2,000 Da). In some case, oligomers may be the polymerization product of one or more monomer precursors. In an embodiment, an oligomer or a monomer cannot be considered a polymer in its own right.

As used herein, the terms "telechelic polymer" and "telechelic oligomer" generally refer to a polymer or oligomer the molecules of which are capable of entering, through reactive groups, into further polymerization.

As used herein, the term "reactive diluent" generally refers to a substance which reduces the viscosity of another substance, such as a monomer or curable resin. A reactive diluent may become part of another substance, such as a polymer obtained by a polymerization process. In some examples, a reactive diluent is a curable monomer which, when mixed with a curable resin, reduces the viscosity of the resultant formulation and is incorporated into the polymer that results from polymerization of the formulation.

Oligomer and polymer mixtures can be characterized and differentiated from other mixtures of oligomers and polymers by measurements of molecular weight and molecular weight distributions.

The average molecular weight (M) is the average number of repeating units n times the molecular weight or molar mass ($M_i$) of the repeating unit. The number-average molecular weight ($M_n$) is the arithmetic mean, representing the total weight of the molecules present divided by the total number of molecules.

Photoinitiators described in the present disclosure can include those that can be activated with light and initiate polymerization of the polymerizable components of the formulation. A "photoinitiator", as used herein, may generally refer to a compound that can produce radical species and/or promote radical reactions upon exposure to radiation (e.g., UV or visible light).

The term "biocompatible," as used herein, refers to a material that does not elicit an immunological rejection or detrimental effect, referred herein as an adverse immune response, when it is disposed within an in-vivo biological environment. For example, in embodiments a biological marker indicative of an immune response changes less than 10%, or less than 20%, or less than 25%, or less than 40%, or less than 50% from a baseline value when a human or animal is exposed to or in contact with the biocompatible material. Alternatively, immune response may be determined histologically, wherein localized immune response is assessed by visually assessing markers, including immune cells or markers that are involved in the immune response pathway, in and adjacent to the material. In an aspect, a biocompatible material or device does not observably change immune response as determined histologically. In some embodiments, the disclosure provides biocompatible devices configured for long-term use, such as on the order of weeks to months, without invoking an adverse immune response. Biological effects may be initially evaluated by measurement of cytotoxicity, sensitization, irritation and intracutaneous reactivity, acute systemic toxicity, pyrogenicity, subacute/subchronic toxicity and/or implantation. Biological tests for supplemental evaluation include testing for chronic toxicity.

"Bioinert" refers to a material that does not elicit an immune response from a human or animal when it is disposed within an in-vivo biological environment. For example, a biological marker indicative of an immune response remains substantially constant (plus or minus 5% of a baseline value) when a human or animal is exposed to or in contact with the bioinert material. In some embodiments, the disclosure provides bioinert devices.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. Specific names of compounds are intended to be exemplary, as it is known that one of ordinary skill in the art can name the same compounds differently.

It is noted that as used herein and in the appended claims, the singular forms "a", "an", and "the" include plural reference unless the context clearly dictates otherwise. Thus, for example, reference to "a monomer" includes a plurality of such monomers and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim.

As used herein, the term "group" may refer to a functional group of a chemical compound. Groups of the present compounds refer to an atom or a collection of atoms that are a part of the compound. Groups of the present disclosure may be attached to other atoms of the compound via one or more covalent bonds. Groups may also be characterized with respect to their valence state. The present disclosure includes groups characterized as monovalent, divalent, trivalent, etc. valence states.

As used herein, the term "substituted" refers to a compound (e.g., an alkyl chain) wherein a hydrogen is replaced by another functional group or atom, as described herein.

As used herein, a broken line in a chemical structure can be used to indicate a bond to the rest of the molecule. For example,  in

is used to designate the 1-position as the point of attachment of 1-methylcyclopentate to the rest of the molecule. Alternatively,

in, e.g.

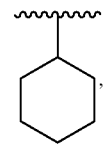

can be used to indicate that the given moiety, the cyclohexyl moiety in this example, is attached to a molecule via the bond that is "capped" with the wavy line.

Alkyl groups include straight-chain, branched and cyclic alkyl groups, unless otherwise defined for a compound or genus of compounds. Alkyl groups include those having from 1 to 30 carbon atoms, unless otherwise defined. Thus, alkyl groups can include small alkyl groups having 1 to 3 carbon atoms, e medium length alkyl groups having from 4-10 carbon atoms, as well as long alkyl groups having more than 10 carbon atoms, particularly those having 10-30 carbon atoms. The term cycloalkyl specifically refers to an alky group having a ring structure such as ring structure comprising 3-30 carbon atoms, optionally 3-20 carbon atoms and optionally 3-10 carbon atoms, including an alkyl group having one or more rings. Cycloalkyl groups include those having a 3-, 4-, 5-, 6-, 7-, 8-, 9- or 10-member carbon ring(s) and particularly those having a 3-, 4-, 5-, 6-, 7- or 8-member ring(s). The carbon rings in cycloalkyl groups can also carry alkyl groups. Cycloalkyl groups can include bicyclic and tricyclic alkyl groups. Alkyl groups are optionally substituted, as described herein. Substituted alkyl groups can include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Unless otherwise defined herein, substituted alkyl groups include fully halogenated or semihalogenated alkyl groups, such as alkyl groups having one or more hydrogens replaced with one or more fluorine atoms, chlorine atoms, bromine atoms and/or iodine atoms. Thus, substituted alkyl groups can include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups. As used herein MeO— refers to $CH_3O$—. Moreover, a thio-alkoxy group, as used herein is an alkyl group that has been modified by linkage to sulfur atom (instead of an oxygen) and can be represented by the formula R—S.

Alkenyl groups include straight-chain, branched and cyclic alkenyl groups. Alkenyl groups include those having 1, 2 or more double bonds and those in which two or more of the double bonds are conjugated double bonds. Unless otherwise defined herein, alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those in which a double bond is in the ring or in an alkenyl group attached to a ring. The term cycloalkenyl specifically refers to an alkenyl group having a ring structure, including an alkenyl group having a 3-, 4-, 5-, 6-, 7-, 8-, 9- or 10-member carbon ring(s) and particularly those having a 3-, 4-, 5-, 6-, 7- or 8-member ring(s). The carbon rings in cycloalkenyl groups can also carry alkyl groups. Cycloalkenyl groups can include bicyclic and tricyclic alkenyl groups. Alkenyl groups are optionally substituted. Unless otherwise defined herein, substituted alkenyl groups include among others those that are substituted with alkyl or aryl groups, which groups in turn can be optionally substituted. Specific alkenyl groups include ethenyl, prop-1-enyl, prop-2-enyl, cyclo-prop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups can include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogen atoms replaced with one or more fluorine atoms.

Aryl groups include groups having one or more 5-, 6-, 7- or 8-membered aromatic rings, including heterocyclic aromatic rings. The term heteroaryl specifically refers to aryl groups having at least one 5-, 6-, 7- or 8-member heterocyclic aromatic rings. Aryl groups can contain one or more fused aromatic rings, including one or more fused heteroaromatic rings, and/or a combination of one or more aromatic rings and one or more nonaromatic rings that may be fused or linked via covalent bonds. Heterocyclic aromatic rings can include one or more N, O, or S atoms in the ring. Heterocyclic aromatic rings can include those with one, two or three N atoms, those with one or two O atoms, and those with one or two S atoms, or combinations of one or two or three N, O or S atoms. Aryl groups are optionally substituted. Substituted aryl groups include among others those that are substituted with alkyl or alkenyl groups, which groups in turn can be optionally substituted. Specific aryl groups include phenyl, biphenyl groups, pyrrolidinyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic group, including monovalent, divalent and polyvalent groups, of the aromatic and heterocyclic aromatic groups listed herein provided in a covalently bonded configuration in the compounds of the disclosure at any suitable point of attachment. In some embodiments, aryl groups contain between 5 and 30 carbon atoms. In some embodiments, aryl groups contain one aromatic or heteroaromatic six-member ring and one or more additional five- or six-member aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl groups having one or more hydrogens replaced with one or more fluorine atoms, chlorine atoms, bromine atoms and/or iodine atoms.

As used herein, the terms "alkylene" and "alkylene group" are used synonymously and refer to a divalent group "—$CH_2$—" derived from an alkyl group as defined herein. The disclosure includes compounds having one or more alkylene groups. Alkylene groups in some compounds function as attaching and/or spacer groups. Compounds of the disclosure may have substituted and/or unsubstituted $C_1$-$C_{20}$ alkylene, $C_1$-$C_{10}$ alkylene and $C_1$-$C_6$ alkylene groups.

As used herein, the terms "cycloalkylene" and "cycloalkylene group" are used synonymously and refer to a divalent group derived from a cycloalkyl group as defined herein. The disclosure includes compounds having one or more cycloalkylene groups. Cycloalkyl groups in some compounds function as attaching and/or spacer groups. Compounds of the disclosure may have substituted and/or unsubstituted $C_3$-$C_{20}$ cycloalkylene, $C_3$-$C_{10}$ cycloalkylene and $C_3$-$C_5$ cycloalkylene groups.

As used herein, the terms "arylene" and "arylene group" are used synonymously and refer to a divalent group derived from an aryl group as defined herein. The disclosure includes compounds having one or more arylene groups. In some embodiments, an arylene is a divalent group derived from an aryl group by removal of hydrogen atoms from two intra-ring carbon atoms of an aromatic ring of the aryl group. Arylene groups in some compounds function as attaching and/or spacer groups. Arylene groups in some compounds function as chromophore, fluorophore, aromatic antenna, dye and/or imaging groups. Compounds of the disclosure include substituted and/or unsubstituted $C_3$-$C_{30}$ arylene, $C_3$-$C_{20}$ arylene, $C_3$-$C_{10}$ arylene and $C_1$-$C_5$ arylene groups.

As used herein, the terms "heteroarylene" and "heteroarylene group" are used synonymously and refer to a divalent group derived from a heteroaryl group as defined herein.

The disclosure includes compounds having one or more heteroarylene groups. In some embodiments, a heteroarylene is a divalent group derived from a heteroaryl group by removal of hydrogen atoms from two intra-ring carbon atoms or intra-ring nitrogen atoms of a heteroaromatic or aromatic ring of the heteroaryl group. Heteroarylene groups in some compounds function as attaching and/or spacer groups. Heteroarylene groups in some compounds function as chromophore, aromatic antenna, fluorophore, dye and/or imaging groups. Compounds of the disclosure include substituted and/or unsubstituted $C_3$-$C_{30}$ heteroarylene, $C_3$-$C_{20}$ heteroarylene, $C_1$-$C_{10}$ heteroarylene and $C_3$-$C_5$ heteroarylene groups.

As used herein, the terms "alkenylene" and "alkenylene group" are used synonymously and refer to a divalent group derived from an alkenyl group as defined herein. The invention includes compounds having one or more alkenylene groups. Alkenylene groups in some compounds function as attaching and/or spacer groups. Compounds of the disclosure include substituted and/or unsubstituted $C_2$-$C_{20}$ alkenylene, $C_2$-$C_{10}$ alkenylene and $C_2$-$C_5$ alkenylene groups.

As used herein, the terms "cycloalkenylene" and "cycloalkenylene group" are used synonymously and refer to a divalent group derived from a cycloalkenyl group as defined herein. The disclosure includes compounds having one or more cycloalkenylene groups. Cycloalkenylene groups in some compounds function as attaching and/or spacer groups. Compounds of the disclosure include substituted and/or unsubstituted $C_3$-$C_{20}$ cycloalkenylene, $C_3$-$C_{10}$ cycloalkenylene and $C_3$-$C_5$ cycloalkenylene groups.

As used herein, the terms "alkynylene" and "alkynylene group" are used synonymously and refer to a divalent group derived from an alkynyl group as defined herein. The disclosure includes compounds having one or more alkynylene groups. Alkynylene groups in some compounds function as attaching and/or spacer groups. Compounds of the disclosure include substituted and/or unsubstituted $C_2$-$C_{20}$ alkynylene, $C_2$-$C_{10}$ alkynylene and $C_2$-$C_5$ alkynylene groups.

As used herein, the terms "halo" and "halogen" can be used interchangeably and refer to a halogen group such as a fluoro (—F), chloro (—Cl), bromo (—Br) or iodo (—I)

The term "heterocyclic" refers to ring structures containing at least one other kind of atom, in addition to carbon, in the ring. Examples of such heteroatoms include nitrogen, oxygen and sulfur. Heterocyclic rings include heterocyclic alicyclic rings and heterocyclic aromatic rings. Examples of heterocyclic rings include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. Atoms of heterocyclic rings can be bonded to a wide range of other atoms and functional groups, for example, provided as substituents.

The term "carbocyclic" refers to ring structures containing only carbon atoms in the ring. Carbon atoms of carbocyclic rings can be bonded to a wide range of other atoms and functional groups, for example, provided as substituents.

The term "alicyclic ring" refers to a ring, or plurality of fused rings, that is not an aromatic ring. Alicyclic rings include both carbocyclic and heterocyclic rings.

The term "aromatic ring" refers to a ring, or a plurality of fused rings, that includes at least one aromatic ring group. The term aromatic ring includes aromatic rings comprising carbon, hydrogen and heteroatoms. Aromatic ring includes carbocyclic and heterocyclic aromatic rings. Aromatic rings are components of aryl groups.

The term "fused ring" or "fused ring structure" refers to a plurality of alicyclic and/or aromatic rings provided in a fused ring configuration, such as fused rings that share at least two intra ring carbon atoms and/or heteroatoms.

As used herein, the term "alkoxyalkyl" refers to a substituent of the formula alkyl-O-alkyl.

As used herein, the term "polyhydroxyalkyl" refers to a substituent having from 2 to 12 carbon atoms and from 2 to 5 hydroxyl groups, such as the 2,3-dihydroxypropyl, 2,3,4-trihydroxybutyl or 2,3,4,5-tetrahydroxypentyl residue.

As used herein, the term "polyalkoxyalkyl" refers to a substituent of the formula alkyl-(alkoxy)n-alkoxy wherein n is an integer from 1 to 10, e.g., 1 to 4, and in some embodiments 1 to 3.

The term "heteroalkyl", as used herein, generally refers to an alkyl, alkenyl or alkynyl group as defined herein, wherein at least one carbon atom of the alkyl group is replaced with a heteroatom. In some instances, heteroalkyl groups may contain from 1 to 18 non-hydrogen atoms (carbon and heteroatoms) in the chain, or from 1 to 12 non-hydrogen atoms, or from 1 to 6 non-hydrogen atoms, or from 1 to 4 non-hydrogen atoms. Heteroalkyl groups may be straight or branched, and saturated or unsaturated. Unsaturated heteroalkyl groups have one or more double bonds and/or one or more triple bonds. Heteroalkyl groups may be unsubstituted or substituted. Exemplary heteroalkyl groups include, but are not limited to, alkoxyalkyl (e.g., methoxymethyl), and aminoalkyl (e.g., alkylaminoalkyl and dialkylaminoalkyl). Heteroalkyl groups may be optionally substituted with one or more substituents.

The term "carbonyl", as used herein, for example in the context of $C_{1-6}$ carbonly substituents, generally refers to a carbon chain of given length (e.g, $C_{1-6}$), wherein each of the carbon atom of a given carbon chain can form the carbonyl bond, as long as it chemically feasible in terms of the valence state of that carbon atom. Thus, in some instance, the "$C_{1-6}$ carbonly" substituent refers to a carbon chain of between 1 and 6 carbon atoms, and either the terminal carbon contains the carbonyl functionality, or an inner carbon contains the carbonyl functionality, in which case the substituent could be described as a ketone. The term "carboxyl", as used herein, for example in the context of $C_{1-6}$ carboxyl substituents, generally refers to a carbon chain of given length (e.g, $C_{1-6}$), wherein a terminal carbon contains the carboxyl functionality, unless otherwise defined herein.

As to any of the groups described herein that contain one or more substituents, it is understood that such groups do not contain any substitution or substitution patterns which are sterically impractical and/or synthetically non-feasible. In addition, the compounds of this disclosure include all stereochemical isomers arising from the substitution of these compounds.

Unless otherwise defined herein, optional substituents for any alkyl, alkenyl and aryl group includes substitution with one or more of the following substituents, among others:
  halogen, including fluorine, chlorine, bromine or iodine;
  pseudohalides, including —CN, —OCN (cyanate), —NCO (isocyanate), —SCN (thiocyanate) and —NCS (isothiocyanate);
  —COOR, where R is a hydrogen or an alkyl group or an aryl group and more specifically where R is a methyl, ethyl, propyl, butyl, or phenyl group all of which groups are optionally substituted;
  —COR, where R is a hydrogen or an alkyl group or an aryl group and more specifically where R is a methyl, ethyl, propyl, butyl, or phenyl group all of which groups are optionally substituted;
  —CON(R)$_2$, where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;
  —OCON(R)$_2$, where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;
  —N(R)$_2$, where each R, independently of each other R, is a hydrogen, or an alkyl group, or an acyl group or an aryl group and more specifically where R is a methyl, ethyl, propyl, butyl, phenyl or acetyl group, all of which are optionally substituted; and where R and R can form a ring that can contain one or more double bonds and can contain one or more additional carbon atoms;
  —SR, where R is hydrogen or an alkyl group or an aryl group and more specifically where R is hydrogen, methyl, ethyl, propyl, butyl, or a phenyl group, which are optionally substituted;
  —SO$_2$R, or —SOR, where R is an alkyl group or an aryl group and more specifically where R is a methyl, ethyl, propyl, butyl, or phenyl group, all of which are optionally substituted;
  —OCOOR, where R is an alkyl group or an aryl group;
  —SO$_2$N(R)$_2$, where each R, independently of each other R, is a hydrogen, or an alkyl group, or an aryl group all of which are optionally substituted and wherein R and R can form a ring that can contain one or more double bonds and can contain one or more additional carbon atoms; and
  —OR, where R is H, an alkyl group, an aryl group, or an acyl group all of which are optionally substituted. In a particular example R can be an acyl yielding —OCOR", wherein R" is a hydrogen or an alkyl group or an aryl group and more specifically where R" is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

As to any of the above groups that contain one or more substituents, it is understood that such groups do not contain any substitution or substitution patterns which are sterically impractical and/or synthetically non-feasible. In addition, the compounds of this disclosure include all stereochemical isomers arising from the substitution of these compounds.

I. Pendant Groups

In various embodiments, a compound to be recovered from a polymeric material (e.g., one that is part of a medical device) using the herein disclosed methods and processes can be a monomeric, oligomeric, and/or polymeric compound. In some embodiments, a compound to be recovered from a polymeric material (e.g., one that is part of a medical device) using the herein disclosed methods and processes can be any aliphatic, cyclo-aliphatic, or aromatic compound with a molecular weight of less than about 1,000 Da, 750 Da, or less than about 500 Da, but no less than about 25 Da.

Thus, in some embodiments, a pendant group of this disclosure is a compound according to Formula (I) (the "⤳" indicates a linkage to a polymer backbone and the bond that may be cleaved to recover the compound as described herein):

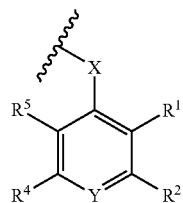
(I)

wherein,
X is O, S or NH;
Y is N or $CR^3$;
$R^1$, $R^2$, $R^3$, $R^4$, and $R^5$ are each independently H, substituted or unsubstituted $C_{1-6}$ alkyl, substituted or unsubstituted $C_{1-6}$ heteroalkyl, substituted or unsubstituted $C_{1-6}$ alkoxy, substituted or unsubstituted $C_{1-6}$ thioalkoxy, substituted or unsubstituted $C_{1-6}$ carbonyl, substituted or unsubstituted $C_{1-6}$ carboxyl, substituted or unsubstituted cyclo($C_{3-8}$) alkyl, substituted or unsubstituted cyclo($C_{3-8}$) heteroalkyl, substituted or unsubstituted aryl, or substituted or unsubstituted heteroaryl, or $R^4$ and $R^5$ together form a 4-, 5-, 6-, 7-, or 8-membered ring selected from substituted or unsubstituted cyclo($C_{4-8}$) alkyl, substituted or unsubstituted cyclo ($C_{4-8}$) heteroalkyl, substituted or unsubstituted aryl, or substituted or unsubstituted heteroaryl.

In various instances, X is O. In some cases, Y is $CR^3$, and $R^2$, $R^3$ and $R^4$ are H. In such instances, $R^1$ and $R^5$ may not be simultaneously H. In some instances, $R^1$, $R^5$, or both $R^1$ and $R^5$ are methoxy.

Hence, in some instances, the pendant group to be recovered can be a compound selected from the group consisting of (the "⤳" indicates a linkage to a polymer backbone and the bond that may be cleaved to recover the compound as described herein):

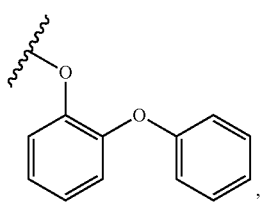
(1)

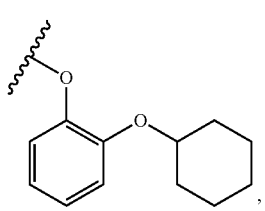
(2)

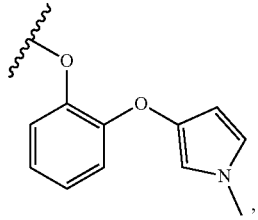
(3)

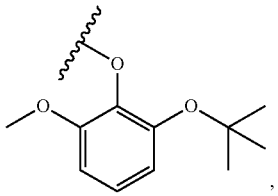
(4)

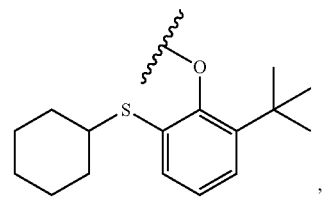
(5)

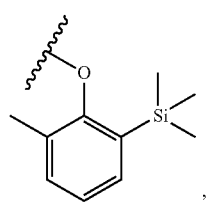
(6)

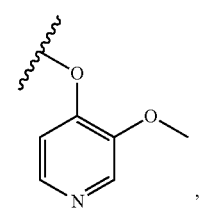
(7)

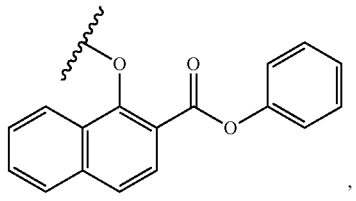
(8)

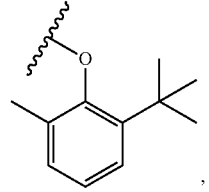
(9)

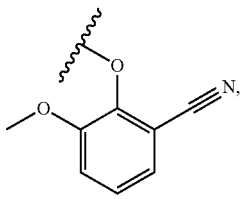
(10)

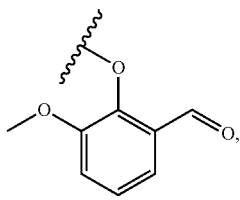
(11)

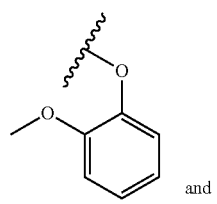
and
(12)

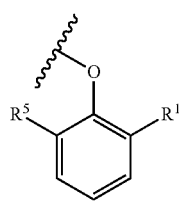
(13)

In some embodiments, the pendant group is a compound according to Formula (II):

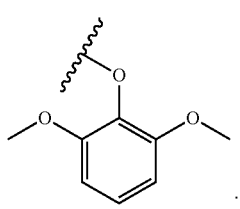
(II)

wherein,
R$^1$ and R$^5$ are each independently H, substituted or unsubstituted C$_{1-6}$ alkyl, substituted or unsubstituted C$_{1-6}$ heteroalkyl, substituted or unsubstituted C$_{1-6}$ alkoxy, substituted or unsubstituted C$_{1-6}$ thioalkoxy, substituted or unsubstituted C$_{1-6}$ carbonyl, substituted or unsubstituted C$_{1-6}$ carboxyl, substituted or unsubstituted cyclo(C$_{3-8}$) alkyl, substituted or unsubstituted cyclo(C$_{3-8}$) heteroalkyl, substituted or unsubstituted aryl, or substituted or unsubstituted heteroaryl, but not simultaneously H. In some cases, R$^1$ and R$^5$ are each independently H, substituted or unsubstituted C$_{1-6}$ alkoxy. In some cases, R$^1$ and R$^5$ are both methoxyl, or R$^1$ is H and R$^5$ is methoxyl.

In various embodiments, a pendant group to be recovered herein can be a compound according to Formulas (III) or (IV) (the "⁓" indicates a linkage to a polymer backbone and the bond that may be cleaved to recover the compound as described herein):

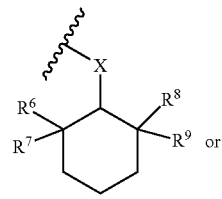
(III)

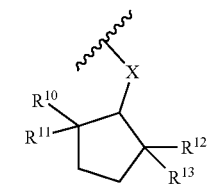
(IV)

wherein
X is O, S or NH;
R$^6$, R$^7$, R$^8$, R$^9$, R$^{10}$, R$^{11}$, R$^{12}$ and R$^{13}$ are each independently H, substituted or unsubstituted C$_{1-6}$ alkyl, substituted or unsubstituted C$_{1-6}$ heteroalkyl, substituted or unsubstituted C$_{1-6}$ alkoxy, substituted or unsubstituted C$_{1-6}$ thioalkoxy, substituted or unsubstituted C$_{1-6}$ carbonyl, substituted or unsubstituted C$_{1-6}$ carboxyl, or —Y—(CH$_2$)$_a$—R$^{14}$;
Y is a bond, O, or S;
a is an integer from 0 to 6; and
R$^{14}$ is substituted or unsubstituted cyclo(C$_{3-8}$) alkyl, substituted or unsubstituted cyclo(C$_{3-8}$) heteroalkyl, substituted or unsubstituted aryl, or substituted or unsubstituted heteroaryl.

In such instances, the pendant group can be selected from the group consisting of (the "⁓" indicates a linkage to a polymer backbone and the bond that may be cleaved to recover the compound as described herein):

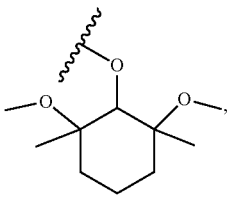
(14)

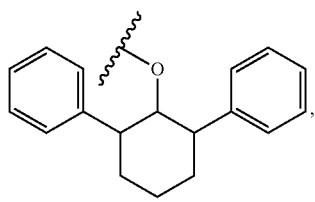
(15)

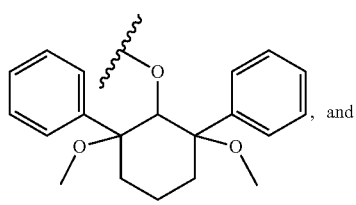
and
(16)

(17)

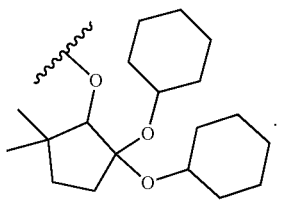

(19)

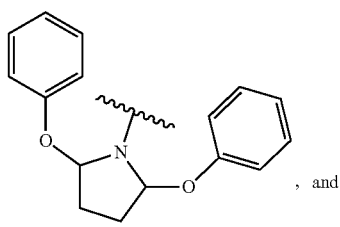
, and (20)

In various embodiments, a pendant group to be recovered herein can be a compound according to Formulas (V)-(VII) (the "⁀" indicates a linkage to a polymer backbone and the bond that may be cleaved to recover the compound as described herein):

(V)
(VI)
(VII)

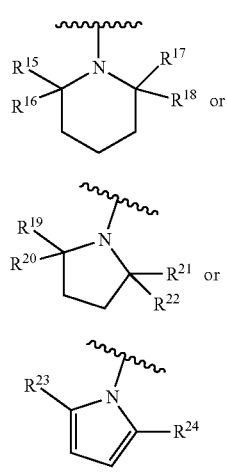

In some embodiments, any one or more of $R^1$-$R^{25}$ can be substituted by a halogen, OH, $NH_2$, $NH(C_{1-6}$ alkyl), $N(C_{1-6}$ alkyl)($C_{1-6}$ alkyl), or $C_{1-3}$ alkyl.

In yet other embodiments, a pendant group herein can comprise an aliphatic, or multi-cyclic (either aliphatic or aromatic) moiety coupled to a backbone of a polymer. In such instances, a pendant group can be a compound of the following structure, or a derivative thereof:

(21)

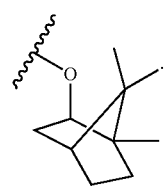

wherein:

$R^{15}$, $R^{16}$, $R^{17}$, $R^{18}$, $R^{19}$, $R^{20}$, $R^{21}$, $R^{22}$, $R^{23}$ and $R^{24}$ are each independently H, substituted or unsubstituted $C_{1-6}$ alkyl, substituted or unsubstituted $C_{1-6}$ heteroalkyl, substituted or unsubstituted $C_{1-6}$ alkoxy, substituted or unsubstituted $C_{1-6}$ thioalkoxy, substituted or unsubstituted $C_{1-6}$ carbonyl, substituted or unsubstituted $C_{1-6}$ carboxyl, or —Z—$(CH_2)_b$—$R^{25}$.

Z is a bond, O, or S;

b is an integer from 0 to 6; and $R^{25}$ is substituted or unsubstituted cyclo($C_{3-8}$) alkyl, substituted or unsubstituted cyclo($C_{3-8}$) heteroalkyl, substituted or unsubstituted aryl, or substituted or unsubstituted heteroaryl.

In such instances, the polymerizable monomer can be selected from the group consisting of (the "⁀" indicates a linkage to a polymer backbone and the bond that may be cleaved to recover the compound as described herein):

(18)

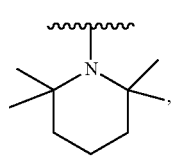

II. Methods of Recovering and Recycling Pendant Groups from a Polymer

The present disclosure provides methods and processes for the recovery, reuse and/or recycling of various molecular components and building blocks present in an oligomer or polymer. In various embodiments, provided herein are methods and processes for the recovery, reuse and/or recycling of pendant groups from an oligomer or polymer, e.g., an oligomer or polymer that is part of a polymeric material, or from a device comprising a polymeric material. In various instances, the device from which a compound, e.g., a pendant group, can be recovered can be a medical device. The medical device can be an orthodontic appliance, such as an aligner, an expande, or a spacer.

Upon recovery and purification, the compound (e.g., pendant group) can be reintroduced into a synthetic framework to produce monomers, oligomers, and/or polymers comprising the recovered compound. The compound to be recovered, reused and recycled can be any aliphatic, cycloaliphatic, or aromatic compound, as further described herein. In various embodiments, the compound to be recovered, reused and recycled has a molecular weight of less than about 1,000 Da, 750 Da, or less than 500 Da, but no less than 25 Da.

In some embodiments, provided herein is a method of recovering a pendant group from a polymer, the method comprising: (i) providing the polymer comprising the pendant group of any one of Formulas (I)-(VII) described herein; (ii) hydrolyzing a bond coupling the pendant group to the backbone of the polymer to produce a mixture; and (iii) recovering the pendant group from the mixture.

In some embodiments, provided herein is a method for recovering a pendant group from a polymer, the method comprising: providing the polymer comprising a synthetic polymer backbone; cleaving a bond coupling the pendant group to the synthetic polymer backbone to produce a mixture; and recovering the pendant group from the mixture. In various embodiments, the pendant group is a compound according to any one of Formulas (I)-(VII) described herein.

In some embodiments, the pendant group to be recovered herein is a compound according to Formula (I). In other cases, the pendant group to be recovered herein is any one or more of compounds 1-21 as further described herein.

Further provided herein are processes for recovering a pendant group from a polymer, comprising: (i) providing a curable composition; (ii) curing the curable composition to generate a polymer comprising a pendant group; (iii) subjecting the polymer to reaction conditions to cleave a bond coupling the pendant group to the backbone of the polymer; and (iv) generating a mixture comprising the pendant group. In some cases, such process produces a polymer or polymeric material for further down-stream processing, e.g., to generate a medical device, and a portion (e.g., about 1%, 2%, 3%, 5%, or 10%) of the cured polymer or polymeric material, if not used for further processing, can be used to recover various components from the polymer or polymeric material, such as a pendant group as described herein. Hence, the processes of the present disclosure also aim to reduce waste that is generated in various device fabrication processes, by recycling and reusing at least a portion of the material that may otherwise be discarded as waste.

In various embodiments, the bond attaching the pendant group to the polymer backbone can be an ester bond, an amide, an ether, a thioether, a thioester, a carbonyl, or any derivative of such bond, e.g., a urea group, a thiourea, etc.

In some instances, the cleaving of the bond can comprise any suitable bond cleavage mechanism known in the art. In some cases, a bond can be cleaved using an elevated temperature (e.g., pyrolysis), an acid such as an inorganic acid, a base such as an inorganic base, or a combination thereof. In various cases, cleaving the bond coupling the pendant group to the synthetic polymer backbone comprises hydrolyzing the bond. In some instances, the hydrolyzing is performed using a base. The base can be an inorganic base, such as an alkali metal or earth alkali metal base (e.g., hydroxide). In various instances, the bond to be hydrolyzed is an ester bond and the base used for the hydrolysis is sodium hydroxide.

Hence, in some embodiments, provided herein are methods and processes for recovering a pendant group from a polymer, the method comprising hydrolyzing a bond coupling the pendant group to the backbone of the polymer. In various instances, the bond is an ester bond, or a derivative thereof (e.g., a thioester). In some instances, the hydrolyzing comprises base-mediated hydrolysis, enzyme-mediated hydrolysis, or a combination thereof. In some cases, the hydrolyzing can be conducted at an elevated temperature, e.g., a temperature >25° C. The elevated temperature can be from about 30° C. to about 150° C., e.g., about 35° C., 40° C., 45° C., 50° C., 55° C., 60° C., 65° C., 70° C., 75° C., 80° C., 85° C., 90° C., 95° C., 100° C., 110° C., 120° C., 130° C., or about 140° C. In instances where the hydrolysis is, at least in part, base-mediated, such base can be an inorganic base. The inorganic base can be an alkali metal hydroxide. In other instances, an organic base such as an organic amine is used, such as pyridine, triethylamine, etc. In yet other cases, a combination of inorganic and organic bases in used.

As described herein, the cleaving of the bond coupling a pendant group to a backbone of a polymer can produce a mixture. Such mixture can comprise the pendant group, or a certain functionalized form thereof, e.g., a hydroxy form, an amine form, etc., depending on the cleaving mechanism and the reagent(s) and/or reaction conditions used for the cleaving step. As an example, a pendant group of Formula (I) herein is coupled to a polymer backbone via an ester bond, the free pendant monomer following hydrolysis comprises a hydroxy group, e.g., can be described as a phenol derivative. In another example, a pendant group of Formula (I) that comprises a secondary amine instead of the oxygen bound to the aromatic ring is coupled to a polymer backbone via an amide bond, the free pendant monomer following hydrolysis comprises a primary amine group, e.g., can be described as an aniline derivative.

In instances where the compound to be recovered is a pendant group from a polymer, the mixture, in addition to a species of pendant group molecules, can further comprise one or more impurities. In such instances, impurities can generally be defined as any molecule, except solvent, that is not a pendant group. Impurities can include any side product(s) and/or decomposition product(s) generated during the cleaving reaction, e.g., hydrolysis. In some instances, a mixture herein can comprise impurities in an amount up to about 10%, 5%, 3%, 2%, or up to about 1% w/w based on dry solids.

In some embodiments, a method for recovering a compound, e.g., a pendant group from a polymer, can further comprise distilling the mixture. Such distilling can produce a fraction comprising a crude pendant group. Such fraction can comprise the crude pendant group in an amount from about 20% w/w to about 90% w/w, from about 30% w/w to about 80% w/w, from about 40% w/w to about 70% w/w, or from about 50% w/w to about 60% w/w based on dry solids. In various instances, the distilling comprises steam-distillation.

The crude (e.g., distilled) recovered compound, e.g., a crude pendant group as described herein, can be further purified according to the methods and processes described herein. In some instances, purification of a crude compound herein, a pendant group, can comprise using a chromatographic separation system. Such chromatographic separation system can comprise one or more exchange resins that can be arranged in one or more separate columns. A purification step herein can furnish a fraction comprising a recovered compound, e.g., a pendant group, in high purity, e.g., at least about 85%, 90%, 92%, or 94% pure, or very high purity, at least about 96%, 98%, or 99% pure. The purity level can be given as percent weight based on dry solids, or as percent purity based on analytical (e.g., liquid or gas) chromatography. In various cases, a purified pendant group can have a purity of least about 85%, 90%, 92%, 94%, 96%, 98%, or 99% pure based on weight of total dry solids present following evaporation of the solvent/eluent.

In some embodiments, the methods and processes of the present disclosure provide for a recovery yield of at least about 40%, 45%, 50%, 55%, 60%, 65%, 70%, 75%, 80%, 85%, 90%, or at least about 95% of the compound to be recovered from a material herein. In various embodiments, the recovered compound is a pendant group and the material is a polymeric material (e.g., one that is part of a medical device). In such instances, at least about 40%, 45%, 50%, 55%, 60%, 65%, 70%, 75%, 80%, 85%, 90%, or at least about 95% of a pendant group can be recovered based on the amount of pendant groups present in the polymer or polymeric material prior to the recovery.

In various embodiments, a polymer herein comprising a pendant group coupled to its backbone can comprise the following structure (VIII), based on Formula (I) herein as an embodiment (Formulas (II)-(VII) can be used accordingly):

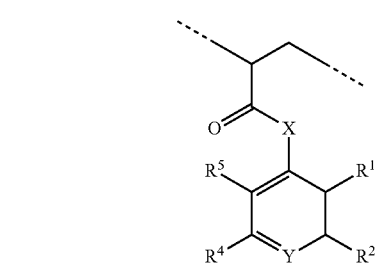

(VIII)

X = O, S, NH wherein,

Y is N or $CR^3$; and $R^1$, $R^2$, $R^3$, $R^4$, and $R^5$ are each independently H, substituted or unsubstituted $C_{1-6}$ alkyl, substituted or unsubstituted $C_{1-6}$ heteroalkyl, substituted or unsubstituted $C_{1-6}$ alkoxy, substituted or unsubstituted $C_{1-6}$ thioalkoxy, substituted or unsubstituted $C_{1-6}$ carbonyl, substituted or unsubstituted $C_{1-6}$ carboxyl, substituted or unsubstituted cyclo($C_{3-8}$) alkyl, substituted or unsubstituted cyclo($C_{3-8}$) heteroalkyl, substituted or unsubstituted aryl, or substituted or unsubstituted heteroaryl, or $R^4$ and $R^5$ together form a 4-, 5-, 6-, 7-, or 8-membered ring selected from substituted or unsubstituted cyclo($C_{4-8}$) alkyl, substituted or unsubstituted cyclo ($C_{4-8}$) heteroalkyl, substituted or unsubstituted aryl, or substituted or unsubstituted heteroaryl.

As described herein, a compound, e.g., a pendant group, can be recovered from a polymer by cleaving a bond coupling the pendant group ("PG") to the backbone of the polymer, as follows:

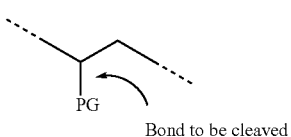

Bond to be cleaved

PG = Pendant Group

A bond coupling the pendant group to the polymer backbone can be cleaved using any known mechanism(s) known in the art and as further described herein.

In some embodiments, however, a pendant group can be recovered from a polymer using hydrolysis, such as base-mediated hydrolysis, as described herein. In such instances, a bond can be cleaved via the following reaction SCHEME 1 (based on Formula (I) herein as an embodiment; Formulas (II)-(VII) can be used interchangeably) to produce a free, or unbound, pendant group:

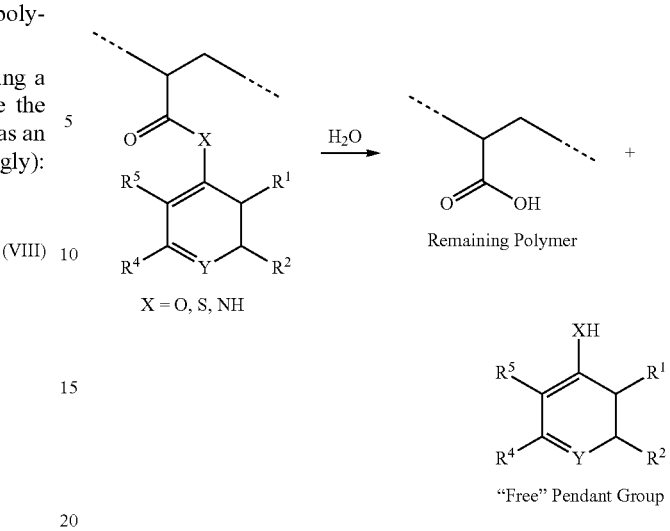

X = O, S, NH wherein,

Y is N or $CR^3$; and $R^1$, $R^2$, $R^3$, $R^4$, and $R^5$ are each independently H, substituted or unsubstituted $C_{1-6}$ alkyl, substituted or unsubstituted $C_{1-6}$ heteroalkyl, substituted or unsubstituted $C_{1-6}$ alkoxy, substituted or unsubstituted $C_{1-6}$ thioalkoxy, substituted or unsubstituted $C_{1-6}$ carbonyl, substituted or unsubstituted $C_{1-6}$ carboxyl, substituted or unsubstituted cyclo($C_{3-8}$) alkyl, substituted or unsubstituted cyclo($C_{3-8}$) heteroalkyl, substituted or unsubstituted aryl, or substituted or unsubstituted heteroaryl, or $R^4$ and $R^5$ together form a 4-, 5-, 6-, 7-, or 8-membered ring selected from substituted or unsubstituted cyclo($C_{4-8}$) alkyl, substituted or unsubstituted cyclo ($C_{4-8}$) heteroalkyl, substituted or unsubstituted aryl, or substituted or unsubstituted heteroaryl.

In some instances, the hydrolysis is base-mediated. In such cases, any inorganic and/or organic base can be used. In various aspects, an alkali metal or earth alkali hydroxide is used, such as LiOH, NaOH, KOH, CsOH, Ca(OH)$_2$, or Mg(OH)$_2$. Suitable solvents can include water, alcohols, or any other polar, aprotic solvent. In some embodiments, base-mediated hydrolysis for recovering a pendant group from a polymer can comprise the reaction outlined in SCHEME 2 (based on Formula (I) herein as an embodiment; Formulas (II)-(VI) can be used interchangeably):

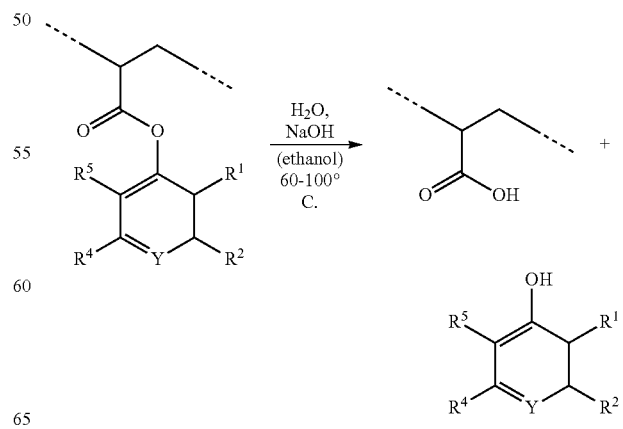

wherein,
Y is N or $CR^3$; and
$R^1$, $R^2$, $R^3$, $R^4$, and $R^5$ are each independently H, substituted or unsubstituted $C_{1-6}$ alkyl, substituted or unsubstituted $C_{1-6}$ heteroalkyl, substituted or unsubstituted $C_{1-6}$ alkoxy, substituted or unsubstituted $C_{1-6}$ thioalkoxy, substituted or unsubstituted $C_{1-6}$ carbonyl, substituted or unsubstituted $C_{1-6}$ carboxyl, substituted or unsubstituted cyclo($C_{3-8}$) alkyl, substituted or unsubstituted cyclo($C_{3-8}$) heteroalkyl, substituted or unsubstituted aryl, or substituted or unsubstituted heteroaryl, or $R^4$ and $R^5$ together form a 4-, 5-, 6-, 7-, or 8-membered ring selected from substituted or unsubstituted cyclo($C_{4-8}$) alkyl, substituted or unsubstituted cyclo ($C_{4-8}$) heteroalkyl, substituted or unsubstituted aryl, or substituted or unsubstituted heteroaryl.

Hence, in some embodiments, a recovered pendant group can be a compound according to Formula (IX):

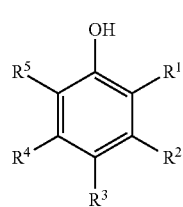

(IX)

wherein,
$R^1$, $R^2$, $R^3$, $R^4$, and $R^5$ are each independently H, substituted or unsubstituted $C_{1-6}$ alkyl, substituted or unsubstituted $C_{1-6}$ heteroalkyl, substituted or unsubstituted $C_{1-6}$ alkoxy, substituted or unsubstituted $C_{1-6}$ thioalkoxy, substituted or unsubstituted $C_{1-6}$ carbonyl, substituted or unsubstituted $C_{1-6}$ carboxyl, substituted or unsubstituted cyclo-($C_{3-8}$) alkyl, substituted or unsubstituted cyclo($C_{3-8}$) heteroalkyl, substituted or unsubstituted aryl, or substituted or unsubstituted heteroaryl.

As described herein, following bond cleavage, the resulting reaction mixture comprising the (unbound) pendant group, as well as any side-products and decomposition products, can be distilled, e.g., steam-distilled, to generate a fraction comprising a crude pendant group. The crude pendant group can then be further purified to produce a pure compound that can be recycled and used to synthesize components for curable resins. The purification can be performed using any known and suitable method, including a chromatography system comprising one or more resins, e.g., ion exchange and/or chiral resins.

III. Methods of Synthesizing Polymerizable Compounds from Recycled Material

Further provided herein are methods for using a purified compound recovered from a polymeric material to synthesize a polymerizable compound that can be used as a component in resins used for fabricating polymeric materials, thereby recycling the compound by reintroducing it into the materials cycle. Such a polymerizable compound generated from a recycled pendant group herein can be used for fabricating polymeric components and materials used in many different industries such as transportation (e.g., planes, trains, boats, automobiles, etc.), hobbyist, prototyping, medical, art and design, microfluidics, molds, among others.

In various embodiments, the compound that is recycled is a pendant group from a polymeric material as described herein. The recycled pendant group can subsequently be purified for further down-stream use. A pendant group herein can comprise or consist of an aliphatic and/or cyclic (either cycloaliphatic and/or aromatic) moiety coupled to a backbone of a polymer. In various embodiments, a pendant group is a compound according to any one of Formulas (I)-(VI). In order to convert such pendant group into a polymerizable compound, any functional group (FG) capable of undergoing a polymerization reaction can be coupled to such pendant group. Such functional group can comprise or consist of any of the following moieties selected from:

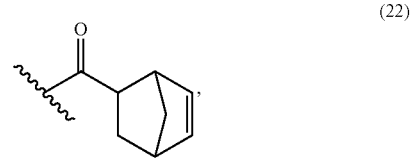

(22)

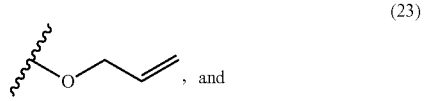

, and (23)

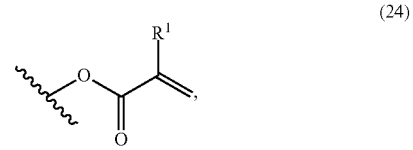

, (24)

or any derivative thereof, wherein "⁓" indicates the location at which the functional group is coupled to a pendant group; and $R^1$ can be H, halogen, or substituted or unsubstituted $C_1$-$C_3$ alkyl.

Generally, any known coupling chemistry can be used to couple a functional group to a pendant group to produce a polymerizable compound, such coupling reactions include nucleophilic substitution or addition reactions, as well as Diels-Alder and click reactions. In some embodiments, a recovered pendant group (based on Formula (I) herein as an embodiment; Formulas (II)-(VI) can be used accordingly) can be modified with a functional group (FG) according to the SCHEME 3:

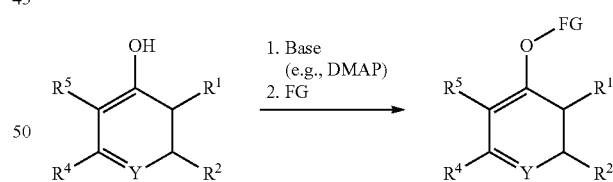

wherein
Y is N or $CR^3$;
FG can be any functional group that can be coupled to the pendant group under the corresponding conditions; and
$R^1$, $R^2$, $R^3$, $R^4$, and $R^5$ are each independently H, substituted or unsubstituted $C_{1-6}$ alkyl, substituted or unsubstituted $C_{1-6}$ heteroalkyl, substituted or unsubstituted $C_{1-6}$ alkoxy, substituted or unsubstituted $C_{1-6}$ thioalkoxy, substituted or unsubstituted $C_{1-6}$ carbonyl, substituted or unsubstituted $C_{1-6}$ carboxyl, substituted or unsubstituted cyclo($C_{3-8}$) alkyl, substituted or unsubstituted cyclo($C_{3-8}$) heteroalkyl, substituted or unsubstituted aryl, or substituted or unsubstituted heteroaryl, or $R^4$ and $R^5$ together form a 4-, 5-, 6-, 7-, or 8-membered ring selected from substituted or unsubstituted cyclo($C_{4-8}$) alkyl, substituted or unsubstituted cyclo ($C_{4-8}$) heteroalkyl, substituted or unsubstituted aryl, or substituted or unsubstituted heteroaryl.

In some embodiments, a recovered pendant group (based on Formula (I) herein as an embodiment; Formulas (II)-(VI) can be used accordingly) can be modified with a functional group comprising an acrylate or methacrylate (epoxide or other functionalities can be used accordingly) to produce a monomer (e.g., a polymerizable monomer) according to SCHEME 4:

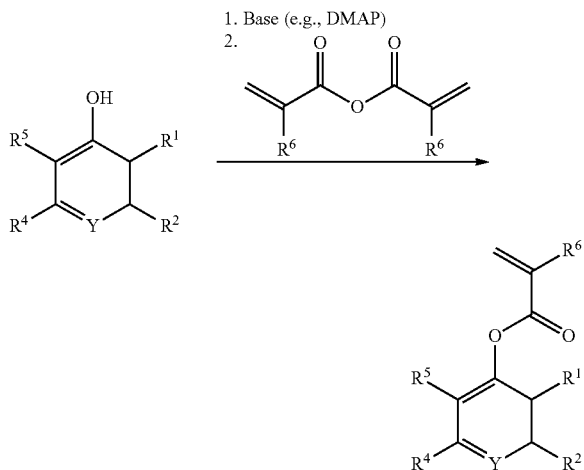

wherein
Y is N or $CR^3$;
$R^1$, $R^2$, $R^3$, $R^4$, and $R^5$ are each independently H, substituted or unsubstituted $C_{1-6}$ alkyl, substituted or unsubstituted $C_{1-6}$ heteroalkyl, substituted or unsubstituted $C_{1-6}$ alkoxy, substituted or unsubstituted $C_{1-6}$ thioalkoxy, substituted or unsubstituted $C_{1-6}$ carbonyl, substituted or unsubstituted $C_{1-6}$ carboxyl, substituted or unsubstituted cyclo($C_{3-8}$) alkyl, substituted or unsubstituted cyclo($C_{3-8}$) heteroalkyl, substituted or unsubstituted aryl, or substituted or unsubstituted heteroaryl, or $R^4$ and $R^5$ together form a 4-, 5-, 6-, 7-, or 8-membered ring selected from substituted or unsubstituted cyclo($C_{4-8}$) alkyl, substituted or unsubstituted cyclo ($C_{4-8}$) heteroalkyl, substituted or unsubstituted aryl, or substituted or unsubstituted heteroaryl; and
$R^6$ is H, halogen, or substituted or unsubstituted $C_{1-3}$ alkyl.

Hence, in some embodiments, a recovered pendant group herein can be used to synthesize a polymerizable monomer according to Formula (X):

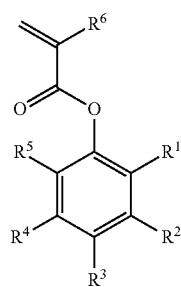

(X)

wherein,
$R^1$, $R^2$, $R^3$, $R^4$, and $R^5$ are each independently H, substituted or unsubstituted $C_{1-6}$ alkyl, substituted or unsubstituted $C_{1-6}$ heteroalkyl, substituted or unsubstituted $C_{1-6}$ alkoxy, substituted or unsubstituted $C_{1-6}$ thioalkoxy, substituted or unsubstituted $C_{1-6}$ carbonyl, substituted or unsubstituted $C_{1-6}$ carboxyl, substituted or unsubstituted cyclo-($C_{3-8}$) alkyl, substituted or unsubstituted cyclo($C_{3-8}$) heteroalkyl, substituted or unsubstituted aryl, or substituted or unsubstituted heteroaryl; and
$R^6$ is H, halogen, or substituted or unsubstituted $C_{1-3}$ alkyl.

In some embodiments, any of such methods can comprise isolating the polymerizable compound comprising a pendant moiety with a chemical yield of at least about 25%, 30%, 40%, 50%, 60%, 70%, 80%, 90%, or at least about 95%, and a chemical purity of at least about 90%, 95%, or 99%. One of skill in the art may appreciate that protecting groups may be necessary for the preparation of certain compounds and may be aware of those conditions compatible with a selected protecting group.

Further provided herein is a method of polymerizing (e.g., photo-curating) a curable composition (e.g., a photo-curable resin) comprising at least one polymerizable compound synthesized from recovered material (e.g., one according to Formula (IX)). In such instances, a polymerizable compounds synthesized from recovered material, e.g., a recovered pendant group, can be used to fabricate polymeric materials used in devices, such as medical devices (e.g., orthodontic devices).

IV. Orthodontic Appliances and Uses Thereof

Provided herein are methods for using recovered material to produce polymeric materials produced, e.g., by using the recovered material as a component of curable resins that can be cured for the fabrication of a medical device, such as an orthodontic appliance (e.g., a dental aligner, a dental expander or a dental spacer). In some instances, the recovered material used to synthesize such medical device can be a pendant group, e.g., a compound according to any one of Formulas (I)-(VI). Any one or more of such compounds can be used as components for viscous or highly viscous photo-curable resins and can result in polymeric materials that can have favorable thermomechanical properties as described herein (e.g., stiffness, stress remaining, etc.) for use in orthodontic appliances, for example, for moving one or more teeth of a patient.

As described herein, the present disclosure also provides a method of repositioning a patient's teeth, the method comprising: (i) generating a treatment plan for the patient, the plan comprising a plurality of intermediate tooth arrangements for moving teeth along a treatment path from an initial tooth arrangement toward a final tooth arrangement; (ii) producing a dental appliance comprising a polymeric material described herein, e.g., a polymeric material that comprises, in a polymerized form, compounds comprising recovered pendant groups, e.g., compounds according to Formulas (I)-(VI); and moving on-track, with the dental appliance, at least one of the patient's teeth toward an intermediate tooth arrangement or the final tooth arrangement. Such dental appliance can be produced using processes that include 3D printing, as further described herein. The method of repositioning a patient's teeth can further comprise tracking progression of the patient's teeth along the treatment path after administration of the dental appliance to the patient, the tracking comprising comparing a current arrangement of the patient's teeth to a planned arrangement of the patient's teeth. In such instances, greater than 60% of the patient's teeth can be on track with the treatment plan after 2 weeks of treatment. In some instances, the dental appliance has a retained repositioning force to the at least one of the patient's teeth after 2 days that is at least 10%, at least 20%, at least 30%, at least 40%, at least 50%, at least 60%, or at least 70% of repositioning force initially provided to the at least one of the patient's teeth.

As used herein, the terms "rigidity" and "stiffness" can be used interchangeably, as are the corresponding terms "rigid" and "stiff." As used herein a "plurality of teeth" encompasses two or more teeth.

In many embodiments, one or more posterior teeth comprises one or more of a molar, a premolar or a canine, and one or more anterior teeth comprising one or more of a central incisor, a lateral incisor, a cuspid, a first bicuspid or a second bicuspid.

In some embodiments, the compositions and methods described herein can be used to couple groups of one or more teeth to each other. The groups of one or more teeth may comprise a first group of one or more anterior teeth and a second group of one or more posterior teeth. The first group of teeth can be coupled to the second group of teeth with the polymeric shell appliances as disclosed herein.

The embodiments disclosed herein are well suited for moving one or more teeth of the first group of one or more teeth or moving one or more of the second group of one or more teeth, and combinations thereof.

The embodiments disclosed herein are well suited for combination with one or more known commercially available tooth moving components such as attachments and polymeric shell appliances. In many embodiments, the appliance and one or more attachments are configured to move one or more teeth along a tooth movement vector comprising six degrees of freedom, in which three degrees of freedom are rotational and three degrees of freedom are translation.

The present disclosure provides orthodontic systems and related methods for designing and providing improved or more effective tooth moving systems for eliciting a desired tooth movement and/or repositioning teeth into a desired arrangement.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof, for example. In some cases, the reinforced composites can comprise a polymer matrix reinforced with ceramic or metallic particles, for example. The appliance can be shaped in many ways, such as with thermoforming or direct fabrication as described herein, for example. Alternatively, or in combination, the appliance can be fabricated with machining such as an appliance fabricated from a block of material with computer numeric control machining. In some cases, the appliance is fabricated using a polymerizable monomer according to the present disclosure, for example, using the monomers as reactive diluents for curable resins.

Turning now to the drawings, in which like numbers designate like elements in the various figures, FIG. 1A illustrates an exemplary tooth repositioning appliance or aligner 100 that can be worn by a patient in order to achieve an incremental repositioning of individual teeth 102 in the jaw. The appliance can include a shell (e.g., a continuous polymeric shell or a segmented shell) having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. In some embodiments, a physical appliance is directly fabricated, e.g., using rapid prototyping fabrication techniques, from a digital model of an appliance. An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, some, most, or even all of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements 104 on teeth 102 with corresponding receptacles or apertures 106 in the appliance 100 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Figure 1B:
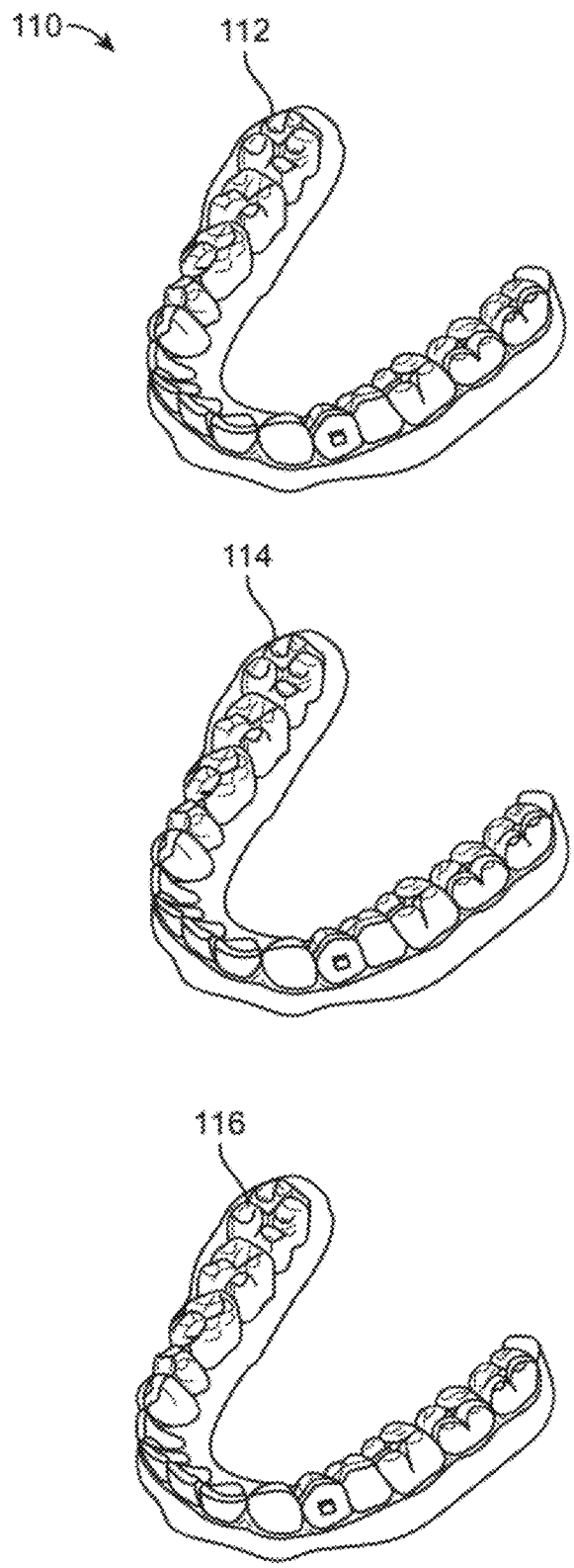
FIG. 1B illustrates a tooth repositioning system, in accordance with embodiments.

FIG. 1B illustrates a tooth repositioning system 110 including a plurality of appliances 112, 114, 116. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 110 can include a first appliance 112 corresponding to an initial tooth arrangement, one or more intermediate appliances 114 corresponding to one or more intermediate arrangements, and a final appliance 116 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

Figure 1C:
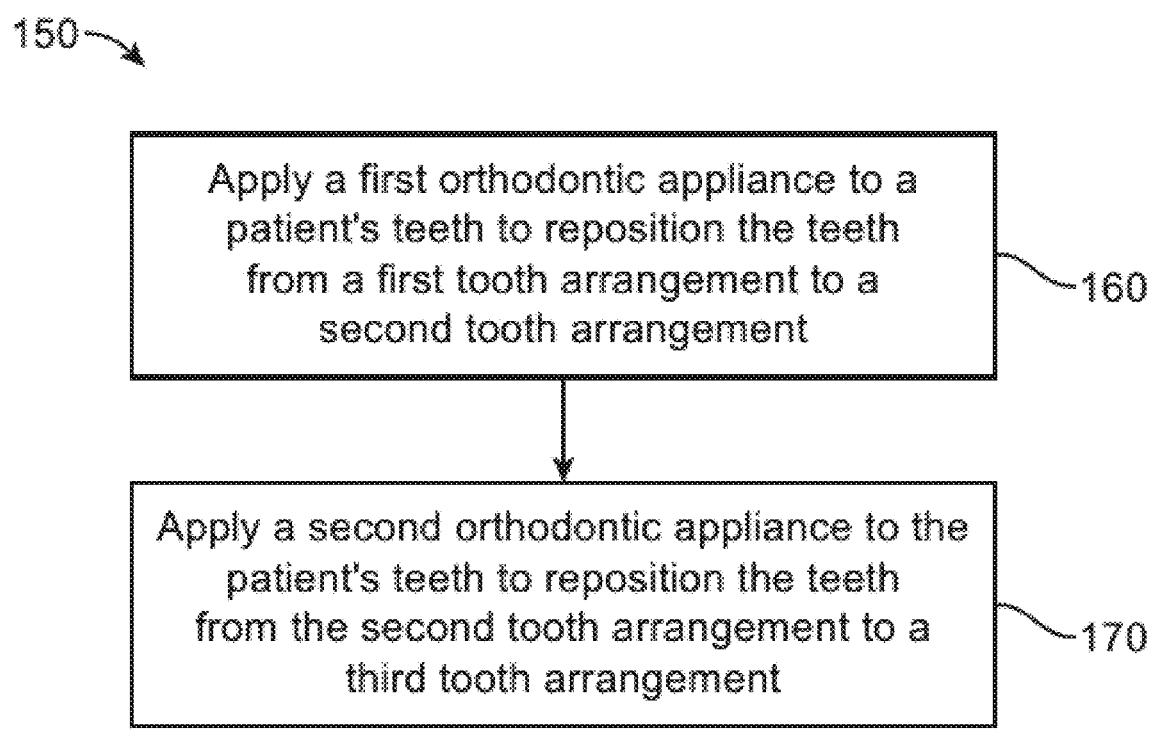
FIG. 1C illustrates a method of orthodontic treatment using a plurality of appliances, in accordance with embodiments.

FIG. 1C illustrates a method 150 of orthodontic treatment using a plurality of appliances, in accordance with embodiments. The method 150 can be practiced using any of the appliances or appliance sets described herein. In step 160, a first orthodontic appliance is applied to a patient's teeth in order to reposition the teeth from a first tooth arrangement to a second tooth arrangement. In step 170, a second orthodontic appliance is applied to the patient's teeth in order to reposition the teeth from the second tooth arrangement to a third tooth arrangement. The method 150 can be repeated as necessary using any suitable number and combination of sequential appliances in order to incrementally reposition the patient's teeth from an initial arrangement to a target arrangement. The appliances can be generated all at the same stage or in sets or batches (e.g., at the beginning of a stage of the treatment), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

The various embodiments of the orthodontic appliances presented herein can be fabricated in a wide variety of ways. In some embodiments, the orthodontic appliances herein (or portions thereof) can be produced using direct fabrication, such as additive manufacturing techniques (also referred to herein as "3D printing," see, e.g., FIG. 5) or subtractive manufacturing techniques (e.g., milling). In some embodiments, direct fabrication involves forming an object (e.g., an orthodontic appliance or a portion thereof) without using a physical template (e.g., mold, mask etc.) to define the object geometry. Additive manufacturing techniques can be categorized as follows: (1) vat photo-polymerization (e.g., stereolithography), in which an object is constructed layer by layer from a vat of liquid photo-polymer resin; (2) material jetting, in which material is jetted onto a build platform using either a continuous or drop on demand (DOD) approach; (3) binder jetting, in which alternating layers of a build material (e.g., a powder-based material) and a binding material (e.g., a liquid binder) are deposited by a print head; (4) fused deposition modeling (FDM), in which material is drawn though a nozzle, heated, and deposited layer by layer; (5) powder bed fusion, including but not limited to direct metal laser sintering (DMLS), electron beam melting (EBM), selective heat sintering (SHS), selective laser melting (SLM), and selective laser sintering (SLS); (6) sheet lamination, including but not limited to laminated object manufacturing (LOM) and ultrasonic additive manufacturing (UAM); and (7) directed energy deposition, including but not limited to laser engineering net shaping, directed light fabrication, direct metal deposition, and 3D laser cladding. For example, stereolithography can be used to directly fabricate one or more of the appliances herein. In some embodiments, stereolithography involves selective polymerization of a photosensitive resin (e.g., a photo-polymer) according to a desired cross-sectional shape using light (e.g., ultraviolet light). The object geometry can be built up in a layer-by-layer fashion by sequentially polymerizing a plurality of object cross-sections. As another example, the appliances herein can be directly fabricated using selective laser sintering. In some embodiments, selective laser sintering involves using a laser beam to selectively melt and fuse a layer of powdered material according to a desired cross-sectional shape in order to build up the object geometry. As yet another example, the appliances herein can be directly fabricated by fused deposition modeling. In some embodiments, fused deposition modeling involves melting and selectively depositing a thin filament of thermoplastic polymer in a layer-by-layer manner in order to form an object. In yet another example, material jetting can be used to directly fabricate the appliances herein. In some embodiments, material jetting involves jetting or extruding one or more materials onto a build surface in order to form successive layers of the object geometry.

Alternatively, or in combination, some embodiments of the appliances herein (or portions thereof) can be produced using indirect fabrication techniques, such as by thermoforming over a positive or negative mold. Indirect fabrication of an orthodontic appliance can involve producing a positive or negative mold of the patient's dentition in a target arrangement (e.g., by rapid prototyping, milling, etc.) and thermoforming one or more sheets of material over the mold in order to generate an appliance shell.

In some embodiments, the direct fabrication methods provided herein build up the object geometry in a layer-by-layer fashion, with successive layers being formed in discrete build steps. Alternatively, or in combination, direct fabrication methods that allow for continuous build-up of an object geometry can be used, referred to herein as "continuous direct fabrication." Various types of continuous direct fabrication methods can be used. As an example, in some embodiments, the appliances herein are fabricated using "continuous liquid interphase printing," in which an object is continuously built up from a reservoir of photo-polymerizable resin by forming a gradient of partially cured resin between the building surface of the object and a polymerization-inhibited "dead zone." In some embodiments, a semi-permeable membrane is used to control transport of a photo-polymerization inhibitor (e.g., oxygen) into the dead zone in order to form the polymerization gradient. Continuous liquid interphase printing can achieve fabrication speeds about 25 times to about 100 times faster than other direct fabrication methods, and speeds about 1000 times faster can be achieved with the incorporation of cooling systems. Continuous liquid interphase printing is described in U.S. Patent Publication Nos. 2015/0097315, 2015/0097316, and 2015/0102532, the disclosures of each of which are incorporated herein by reference in their entirety.

As another example, a continuous direct fabrication method can achieve continuous build-up of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved. Such methods are described in U.S. Pat. No. 7,892,474, the disclosure of which is incorporated herein by reference in its entirety.

In another example, a continuous direct fabrication method can involve extruding a composite material composed of a curable liquid material surrounding a solid strand. The composite material can be extruded along a continuous three-dimensional path in order to form the object. Such methods are described in U.S. Patent Publication No. 2014/0061974, the disclosure of which is incorporated herein by reference in its entirety.

In yet another example, a continuous direct fabrication method utilizes a "heliolithography" approach in which the liquid photo-polymer is cured with focused radiation while the build platform is continuously rotated and raised. Accordingly, the object geometry can be continuously built up along a spiral build path. Such methods are described in U.S. Patent Publication No. 2014/0265034, the disclosure of which is incorporated herein by reference in its entirety.

The direct fabrication approaches provided herein are compatible with a wide variety of materials, including but not limited to one or more of the following: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a poly amide, a polyethylene terephthalate, a polybutylene terephthalate, a polyetherimide, a polyethersulfone, a polytrimethylene terephthalate, a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyamide elastomer, a thermoset material, or combinations thereof. The materials used for direct fabrication can be provided in an uncured form (e.g., as a liquid, resin, powder, etc.) and can be cured (e.g., by photo-polymerization, light curing, gas curing, laser curing, cross-linking, etc.) in order to form an orthodontic appliance or a portion thereof. The properties of the material before curing may differ from the properties of the material after curing. Once cured, the materials herein can exhibit sufficient strength, stiffness, durability, biocompatibility, etc. for use in an orthodontic appliance. The post-curing properties of the materials used can be selected according to the desired properties for the corresponding portions of the appliance.

In some embodiments, relatively rigid portions of the orthodontic appliance can be formed via direct fabrication using one or more of the following materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, and/or a polytrimethylene terephthalate.

In some embodiments, relatively elastic portions of the orthodontic appliance can be formed via direct fabrication using one or more of the following materials: a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, and/or a thermoplastic polyamide elastomer.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated before, during, and/or at the end of each build, and/or at predetermined time intervals (e.g., every $n^{th}$ build, once per hour, once per day, once per week, etc.), depending on the stability of the system. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

Optionally, the direct fabrication methods described herein allow for fabrication of an appliance including multiple materials, referred to herein as "multi-material direct fabrication." In some embodiments, a multi-material direct fabrication method involves concurrently forming an object from multiple materials in a single manufacturing step. For instance, a multi-tip extrusion apparatus can be used to selectively dispense multiple types of materials from distinct material supply sources in order to fabricate an object from a plurality of different materials. Such methods are described in U.S. Pat. No. 6,749,414, the disclosure of which is incorporated herein by reference in its entirety. Alternatively, or in combination, a multi-material direct fabrication method can involve forming an object from multiple materials in a plurality of sequential manufacturing steps. For instance, a first portion of the object can be formed from a first material in accordance with any of the direct fabrication methods herein, then a second portion of the object can be formed from a second material in accordance with methods herein, and so on, until the entirety of the object has been formed.

Direct fabrication can provide various advantages compared to other manufacturing approaches. For instance, in contrast to indirect fabrication, direct fabrication permits production of an orthodontic appliance without utilizing any molds or templates for shaping the appliance, thus reducing the number of manufacturing steps involved and improving the resolution and accuracy of the final appliance geometry. Additionally, direct fabrication permits precise control over the three-dimensional geometry of the appliance, such as the appliance thickness. Complex structures and/or auxiliary components can be formed integrally as a single piece with the appliance shell in a single manufacturing step, rather than being added to the shell in a separate manufacturing step. In some embodiments, direct fabrication is used to produce appliance geometries that would be difficult to create using alternative manufacturing techniques, such as appliances with very small or fine features, complex geometric shapes, undercuts, interproximal structures, shells with variable thicknesses, and/or internal structures (e.g., for improving strength with reduced weight and material usage). For example, in some embodiments, the direct fabrication approaches herein permit fabrication of an orthodontic appliance with feature sizes of less than or equal to about 5 µm, or within a range from about 5 µm to about 50 µm, or within a range from about 20 µm to about 50 µm.

The direct fabrication techniques described herein can be used to produce appliances with substantially isotropic material properties, e.g., substantially the same or similar strengths along all directions. In some embodiments, the direct fabrication approaches herein permit production of an orthodontic appliance with a strength that varies by no more than about 25%, about 20%, about 15%, about 10%, about 5%, about 1%, or about 0.5% along all directions. Additionally, the direct fabrication approaches herein can be used to produce orthodontic appliances at a faster speed compared to other manufacturing techniques. In some embodiments, the direct fabrication approaches herein allow for production of an orthodontic appliance in a time interval less than or equal to about 1 hour, about 30 minutes, about 25 minutes, about 20 minutes, about 15 minutes, about 10 minutes, about 5 minutes, about 4 minutes, about 3 minutes, about 2 minutes, about 1 minutes, or about 30 seconds. Such manufacturing speeds allow for rapid "chair-side" production of customized appliances, e.g., during a routine appointment or checkup.

In some embodiments, the direct fabrication methods described herein implement process controls for various machine parameters of a direct fabrication system or device in order to ensure that the resultant appliances are fabricated with a high degree of precision. Such precision can be beneficial for ensuring accurate delivery of a desired force system to the teeth in order to effectively elicit tooth movements. Process controls can be implemented to account for process variability arising from multiple sources, such as the material properties, machine parameters, environmental variables, and/or post-processing parameters.

Material properties may vary depending on the properties of raw materials, purity of raw materials, and/or process variables during mixing of the raw materials. In many embodiments, resins or other materials for direct fabrication should be manufactured with tight process control to ensure little variability in photo-characteristics, material properties (e.g., viscosity, surface tension), physical properties (e.g., modulus, strength, elongation) and/or thermal properties (e.g., glass transition temperature, heat deflection temperature). Process control for a material manufacturing process can be achieved with screening of raw materials for physical properties and/or control of temperature, humidity, and/or other process parameters during the mixing process. By implementing process controls for the material manufacturing procedure, reduced variability of process parameters and more uniform material properties for each batch of material can be achieved. Residual variability in material properties can be compensated with process control on the machine, as discussed further herein.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated at the end of each build. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

In many embodiments, environmental variables (e.g., temperature, humidity, Sunlight or exposure to other energy/curing source) are maintained in a tight range to reduce variability in appliance thickness and/or other properties. Optionally, machine parameters can be adjusted to compensate for environmental variables.

In many embodiments, post-processing of appliances includes cleaning, post-curing, and/or support removal processes. Relevant post-processing parameters can include purity of cleaning agent, cleaning pressure and/or temperature, cleaning time, post-curing energy and/or time, and/or consistency of support removal process. These parameters can be measured and adjusted as part of a process control scheme. In addition, appliance physical properties can be varied by modifying the post-processing parameters. Adjusting post-processing machine parameters can provide another way to compensate for variability in material properties and/or machine properties.

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled rapid prototyping such as 3D printing, etc.). The computer-based methods presented herein can improve the accuracy, flexibility, and convenience of appliance fabrication.

FIG. 2 illustrates a method 200 for designing an orthodontic appliance to be produced by direct fabrication, in accordance with embodiments. The method 200 can be applied to any embodiment of the orthodontic appliances described herein. Some or all of the steps of the method 200 can be performed by any suitable data processing system or device, e.g., one or more processors configured with suitable instructions.

In step 210, a movement path to move one or more teeth from an initial arrangement to a target arrangement is determined. The initial arrangement can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. From the obtained data, a digital data set can be derived that represents the initial (e.g., pretreatment) arrangement of the patient's teeth and other tissues. Optionally, the initial digital data set is processed to segment the tissue constituents from each other. For example, data structures that digitally represent individual tooth crowns can be produced. Advantageously, digital models of entire teeth can be produced, including measured or extrapolated hidden surfaces and root structures, as well as surrounding bone and soft tissue.

The target arrangement of the teeth (e.g., a desired and intended end result of orthodontic treatment) can be received from a clinician in the form of a prescription, can be calculated from basic orthodontic principles, and/or can be extrapolated computationally from a clinical prescription. With a specification of the desired final positions of the teeth and a digital representation of the teeth themselves, the final position and surface geometry of each tooth can be specified to form a complete model of the tooth arrangement at the desired end of treatment.

Having both an initial position and a target position for each tooth, a movement path can be defined for the motion of each tooth. In some embodiments, the movement paths are configured to move the teeth in the quickest fashion with the least amount of round-tripping to bring the teeth from their initial positions to their desired target positions. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions, so that moving from one point to the next in the sequence does not result in a collision of teeth.

In step 220, a force system to produce movement of the one or more teeth along the movement path is determined. A force system can include one or more forces and/or one or more torques. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

The determination of the force system can include constraints on the allowable forces, such as allowable directions and magnitudes, as well as desired motions to be brought about by the applied forces. For example, in fabricating palatal expanders, different movement strategies may be desired for different patients. For example, the amount of force needed to separate the palate can depend on the age of the patient, as very young patients may not have a fully-formed suture. Thus, in juvenile patients and others without fully-closed palatal sutures, palatal expansion can be accomplished with lower force magnitudes. Slower palatal movement can also aid in growing bone to fill the expanding suture. For other patients, a more rapid expansion may be desired, which can be achieved by applying larger forces. These requirements can be incorporated as needed to choose the structure and materials of appliances; for example, by choosing palatal expanders capable of applying large forces for rupturing the palatal suture and/or causing rapid expansion of the palate. Subsequent appliance stages can be designed to apply different amounts of force, such as first applying a large force to break the suture, and then applying smaller forces to keep the suture separated or gradually expand the palate and/or arch.

The determination of the force system can also include modeling of the facial structure of the patient, such as the skeletal structure of the jaw and palate. Scan data of the palate and arch, such as Xray data or 3D optical scanning data, for example, can be used to determine parameters of the skeletal and muscular system of the patient's mouth, so as to determine forces sufficient to provide a desired expansion of the palate and/or arch. In some embodiments, the thickness and/or density of the mid-palatal suture may be measured, or input by a treating professional. In other embodiments, the treating professional can select an appropriate treatment based on physiological characteristics of the patient. For example, the properties of the palate may also be estimated based on factors such as the patient's age—for example, young juvenile patients will typically require lower forces to expand the suture than older patients, as the suture has not yet fully formed.

In step 230, an arch or palate expander design for an orthodontic appliance configured to produce the force system is determined. Determination of the arch or palate expander design, appliance geometry, material composition, and/or properties can be performed using a treatment or force application simulation environment. A simulation environment can include, e.g., computer modeling systems, biomechanical systems or apparatus, and the like. Optionally, digital models of the appliance and/or teeth can be produced, such as finite element models. The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, CA For creating finite element models and analyzing them, program products from a number of vendors can be used, including finite element analysis packages from ANSYS, Inc., of Canonsburg, PA, and SIMULIA(Abaqus) software products from Dassault Systèmes of Waltham, MA.

Optionally, one or more arch or palate expander designs can be selected for testing or force modeling. As noted above, a desired tooth movement, as well as a force system required or desired for eliciting the desired tooth movement, can be identified. Using the simulation environment, a candidate arch or palate expander design can be analyzed or modeled for determination of an actual force system resulting from use of the candidate appliance. One or more modifications can optionally be made to a candidate appliance, and force modeling can be further analyzed as described, e.g., in order to iteratively determine an appliance design that produces the desired force system.

In step 240, instructions for fabrication of the orthodontic appliance incorporating the arch or palate expander design are generated. The instructions can be configured to control a fabrication system or device in order to produce the orthodontic appliance with the specified arch or palate expander design. In some embodiments, the instructions are configured for manufacturing the orthodontic appliance using direct fabrication (e.g., stereolithography, selective laser sintering, fused deposition modeling, 3D printing, continuous direct fabrication, multi-material direct fabrication, etc.), in accordance with the various methods presented herein. In alternative embodiments, the instructions can be configured for indirect fabrication of the appliance, e.g., by thermoforming.

Method 200 may comprise additional steps: 1) The upper arch and palate of the patient is scanned intraorally to generate three dimensional data of the palate and upper arch; 2) The three dimensional shape profile of the appliance is determined to provide a gap and teeth engagement structures as described herein.

Although the above steps show a method 200 of designing an orthodontic appliance in accordance with some embodiments, a person of ordinary skill in the art will recognize some variations based on the teaching described herein. Some of the steps may comprise sub-steps. Some of the steps may be repeated as often as desired. One or more steps of the method 200 may be performed with any suitable fabrication system or device, such as the embodiments described herein. Some of the steps may be optional, and the order of the steps can be varied as desired.

Figure 3:
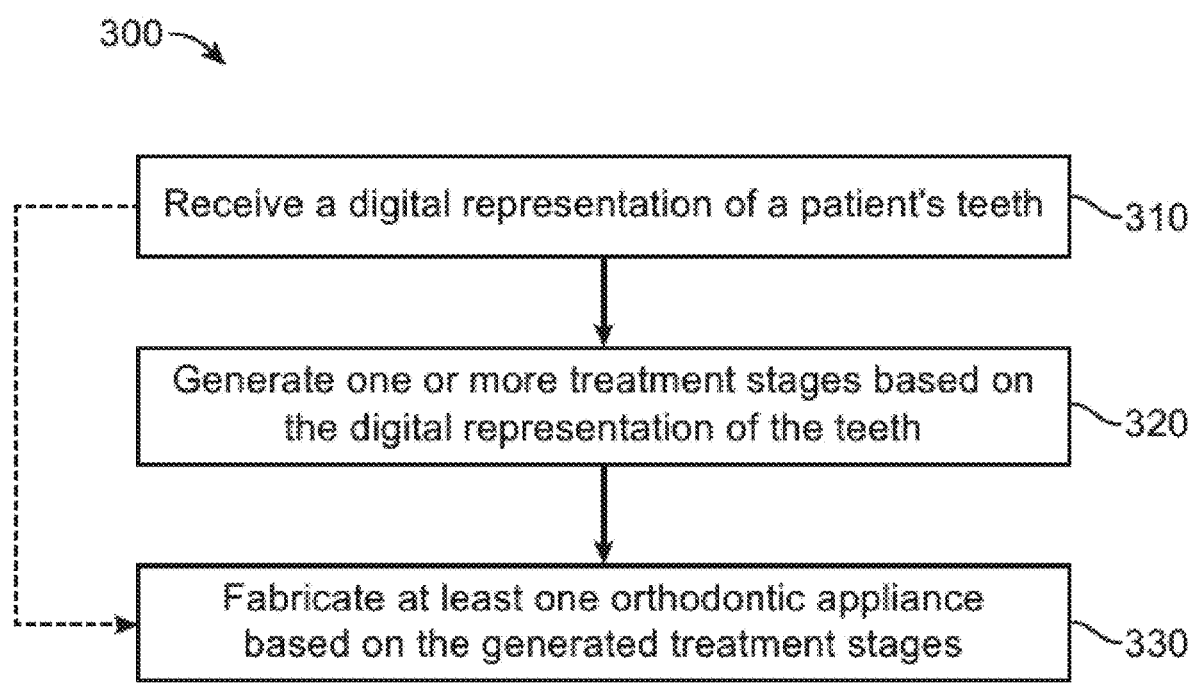
FIG. 3 illustrates a method for digitally planning an orthodontic treatment, in accordance with embodiments.

FIG. 3 illustrates a method 300 for digitally planning an orthodontic treatment and/or design or fabrication of an appliance, in accordance with embodiments. The method 300 can be applied to any of the treatment procedures described herein and can be performed by any suitable data processing system.

In step 310, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In step 320, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In step 330, at least one orthodontic appliance is fabricated based on the generated treatment stages. For example, a set of appliances can be fabricated, each shaped according a tooth arrangement specified by one of the treatment stages, such that the appliances can be sequentially worn by the patient to incrementally reposition the teeth from the initial arrangement to the target arrangement. The appliance set may include one or more of the orthodontic appliances described herein. The fabrication of the appliance may involve creating a digital model of the appliance to be used as input to a computer-controlled fabrication system. The appliance can be formed using direct fabrication methods, indirect fabrication methods, or combinations thereof, as desired.

In some instances, staging of various arrangements or treatment stages may not be necessary for design and/or fabrication of an appliance. As illustrated by the dashed line in FIG. 3, design and/or fabrication of an orthodontic appliance, and perhaps a particular orthodontic treatment, may include use of a representation of the patient's teeth (e.g., receive a digital representation of the patient's teeth 310), followed by design and/or fabrication of an orthodontic appliance based on a representation of the patient's teeth in the arrangement represented by the received representation.

On-Track Treatment

Figure 4:
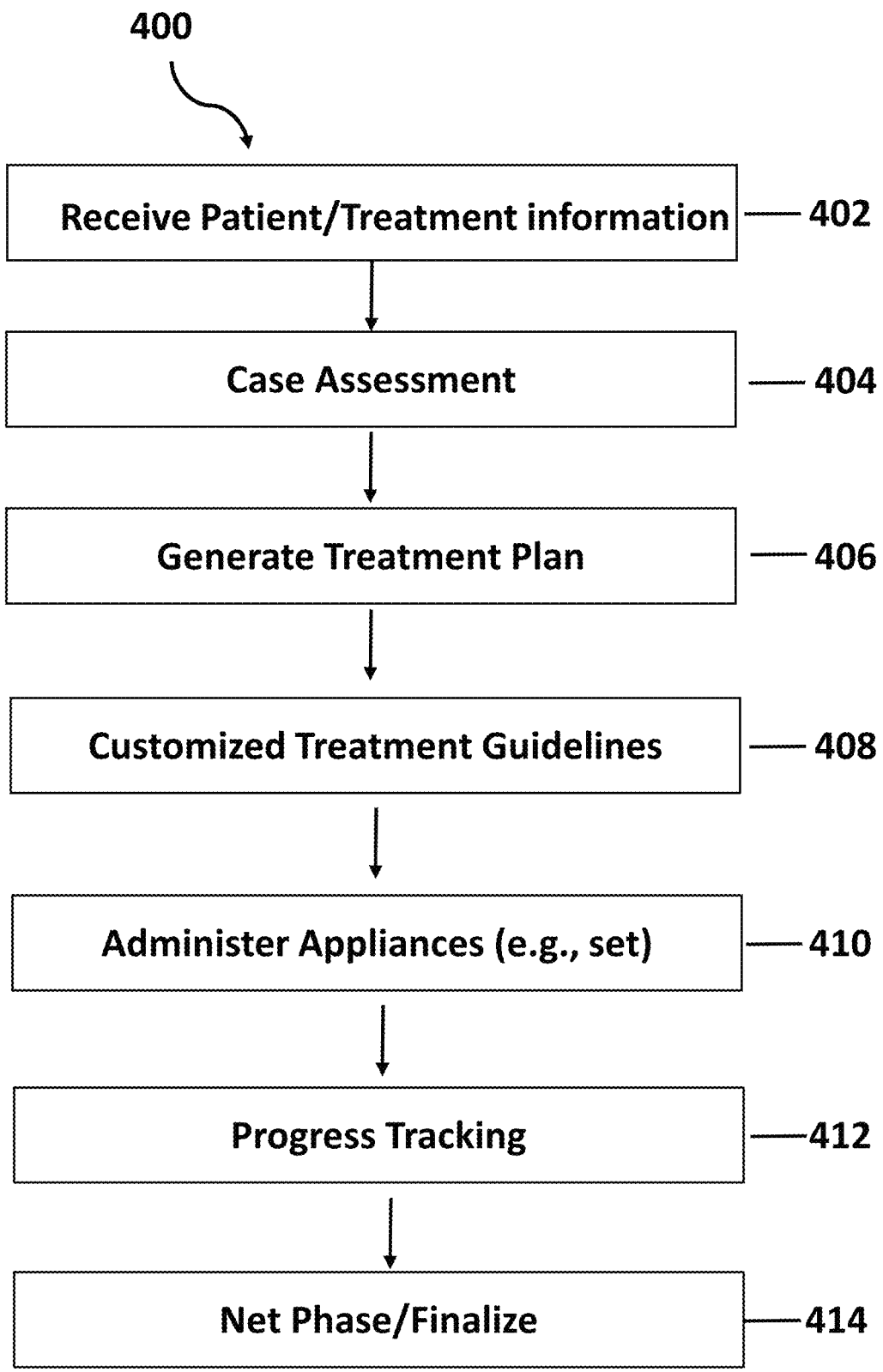
FIG. 4 shows generating and administering treatment according to an embodiment of the present disclosure.

Referring to FIG. 4, a process 400 according to the present disclosure is illustrated. Individual aspects of the process are discussed in further detail below. The process includes receiving information regarding the orthodontic condition of the patient and/or treatment information (402), generating an assessment of the case (404), and generating a treatment plan for repositioning a patient's teeth (406). Briefly, a patient/treatment information includes data comprising an initial arrangement of the patient's teeth, which includes obtaining an impression or scan of the patient's teeth prior to the onset of treatment and can further include identification of one or more treatment goals selected by the practitioner and/or patient. A case assessment can be generated (404) so as to assess the complexity or difficulty of moving the particular patient's teeth in general or specifically corresponding to identified treatment goals, and may further include practitioner experience and/or comfort level in administering the desired orthodontic treatment. In some cases, however, the assessment can include simply identifying particular treatment options (e.g., appointment planning, progress tracking, etc.) that are of interest to the patient and/or practitioner. The information and/or corresponding treatment plan includes identifying a final or target arrangement of the patient's teeth that is desired, as well as a plurality of planned successive or intermediary tooth arrangements for moving the teeth along a treatment path from the initial arrangement toward the selected final or target arrangement.

The process further includes generating customized treatment guidelines (408). The treatment plan may include multiple phases of treatment, with a customized set of treatment guidelines generated that correspond to a phase of the treatment plan. The guidelines can include detailed information on timing and/or content (e.g., specific tasks) to be completed during a given phase of treatment, and can be of sufficient detail to guide a practitioner, including a less experienced practitioner or practitioner relatively new to the particular orthodontic treatment process, through the phase of treatment. Since the guidelines are designed to specifically correspond to the treatment plan and provide guidelines on activities specifically identified in the treatment information and/or generated treatment plan, the guidelines can be customized. The customized treatment guidelines are then provided to the practitioner so as to help instruct the practitioner as how to deliver a given phase of treatment. As set forth above, appliances can be generated based on the planned arrangements and can be provided to the practitioner and ultimately administered to the patient (410). The appliances can be provided and/or administered in sets or batches of appliances, such as 2, 3, 4, 5, 6, 7, 8, 9, or more appliances, but are not limited to any particular administrative scheme. Appliances can be provided to the practitioner concurrently with a given set of guidelines, or appliances and guidelines can be provided separately.

After the treatment according to the plan begins and following administration of appliances to the patient, treatment progress tracking, e.g., by teeth matching, is done to assess a current and actual arrangement of the patient's teeth compared to a planned arrangement (412). If the patient's teeth are determined to be "on-track" and progressing according to the treatment plan, then treatment progresses as planned and treatment progresses to the next stage of treatment (414). If the patient's teeth have substantially reached the initially planned final arrangement, then treatment progresses to the final stages of treatment (414). Where the patient's teeth are determined to be tracking according to the treatment plan, but have not yet reached the final arrangement, the next set of appliances can be administered to the patient.

The threshold difference values of a planned position of teeth to actual positions selected as indicating that a patient's teeth have progressed on-track are provided below in TABLE 1. If a patient's teeth have progressed at or within the threshold values, the progress is considered to be on-track. If a patient's teeth have progressed beyond the threshold values, the progress is considered to be off-track.

TABLE 1

| Type Movement | Difference Actual/Planned |
| --- | --- |
| Rotations | |
| Upper Central Incisors | 9 degrees |
| Upper Lateral Incisors | 11 degrees |
| Lower Incisors | 11 degrees |
| Upper Cuspids | 11 degrees |
| Lower Cuspids | 9.25 degrees |
| Upper Bicuspids | 7.25 degrees |
| Lower First Bicuspid | 7.25 degrees |
| Lower Second Bicuspid | 7.25 degrees |
| Molars | 6 degrees |
| Extrusion | |
| Anterior | 0.75 mm |
| Posterior | 0.75 mm |
| Intrusion | |
| Anterior | 0.75 mm |
| Posterior | 0.75 mm |
| Angulation | |
| Anterior | 5.5 degrees |
| Posterior | 3.7 degrees |
| Inclination | |
| Anterior | 5.5 degrees |
| Posterior | 3.7 degrees |
| Translation | |
| BL Anterior | 0.7 mm |
| BL Posterior Cuspids | 0.9 mm |
| MD Anterior | 0.45 mm |
| MD Cuspids | 0.45 mm |
| MD Posterior | 0.5 mm |

The patient's teeth are determined to be on track by comparison of the teeth in their current positions with teeth in their expected or planned positions, and by confirming the teeth are within the parameter variance disclosed in TABLE 1. If the patient's teeth are determined to be on track, then treatment can progress according to the existing or original treatment plan. For example, a patient determined to be progressing on track can be administered one or more subsequent appliances according to the treatment plan, such as the next set of appliances. Treatment can progress to the final stages and/or can reach a point in the treatment plan where bite matching is repeated for a determination of whether a patient's teeth are progressing as planned or if the teeth are off track.

In some embodiments, as further disclosed herein, this disclosure provides methods of treating a patient using a 3D printed orthodontic appliance. As a non-limiting example, orthodontic appliances comprising crystalline domains, polymer crystals, and/or materials that can form crystalline domains or polymer crystals can be 3D printed and used to reposition a patient's teeth. In certain embodiments, the method of repositioning a patient's teeth (or, in some embodiments, a singular tooth) comprises: generating a treatment plan for the patient, the plan comprising a plurality of intermediate tooth arrangements for moving teeth along a treatment path from an initial arrangement toward a final arrangement; producing a 3D printed orthodontic appliance; and moving on-track, with the orthodontic appliance, at least one of the patient's teeth toward an intermediate arrangement or a final tooth arrangement. In some embodiments, producing the 3D printed orthodontic appliance uses the crystallizable resins disclosed further herein. On-track performance can be determined, e.g., from TABLE 1, above.

In some embodiments, the method further comprises tracking the progression of the patient's teeth along the treatment path after administration of the orthodontic appliance. In certain embodiments, the tracking comprises comparing a current arrangement of the patient's teeth to a planned arrangement of the teeth. As a non-limiting example, following the initial administration of the orthodontic appliance, a period of time passes (e.g., two weeks), a comparison of the now-current arrangement of the patient's teeth (i.e., at two weeks of treatment) can be compared with the teeth arrangement of the treatment plan. In some embodiments, the progression can also be tracked by comparing the current arrangement of the patient's teeth with the initial configuration of the patient's teeth. The period of time can be, for example, greater than 3 days, greater than 4 days, greater than 5 days, greater than 6 days, greater than 7 days, greater than 8 days, greater than 9 days, greater than 10 days, greater than 11 days, greater than 12 days, greater than 13 days, greater than 2 weeks, greater than 3 weeks, greater than 4 weeks, or greater than 2 months. In some embodiments, the period of time can be from at least 3 days to at most 4 weeks, from at least 3 days to at most 3 weeks, from at least 3 days to at most 2 weeks, from at least 4 days to at most 4 weeks, from at least 4 days to at most 3 weeks, or from at least 4 days to at most 2 weeks. In certain embodiments, the period of time can restart following the administration of a new orthodontic appliance.

In some embodiments, greater than 50%, greater than 55%, greater than 60%, greater than 65%, greater than 70%, greater than 75%, greater than 80%, greater than 85%, greater than 90%, greater than 91%, greater than 92%, greater than 93%, greater than 94%, greater than 95%, greater than 96%, greater than 97%, greater than 98%, or greater than 99% of the patient's teeth are on track with the treatment plan after a period of time of using an orthodontic appliance as disclosed further herein. In some embodiments, the period of time is 3 days, 4 days, 5 days, 6 days, 7 days, 8 days, 9 days, 10 days, 11 days, 12 days, 13 days, 2 weeks, 3 weeks, 4 weeks, or greater than 4 weeks.

As disclosed further herein, orthodontic appliances disclosed herein have advantageous properties, such as increased durability, and an ability to retain resilient forces to a patient's teeth for a prolonged period of time. In some embodiments of the method disclosed above, the 3D printed orthodontic appliance has a retained repositioning force (i.e., the repositioning force after the orthodontic appliance has been applied to or worn by the patient over a period of time), and the retained repositioning force to at least one of the patient's teeth after the period of time is at least 10%, at least 20%, at least 30%, at least 40%, at least 50%, at least 55%, at least 60%, at least 65%, at least 70%, at least 75%, at least 80%, at least 85%, at least 90%, at least 95%, at least 96%, at least 97%, at least 98%, or at least 99% of the repositioning force initially provided to the at least one of the patient's teeth (i.e., with initial application of the orthodontic appliance). In some embodiments, the period of time is 1 day, 2 days, 3 days, 4 days, 5 days, 6 days, 7 days, 8 days, 9 days, 10 days, 11 days, 12 days, 13 days, 2 weeks, 3 weeks, 4 weeks, or greater than 4 weeks. In some embodiments, the repositioning force applied to at least one of the patient's teeth is present for a time period of less than 24 hours, from about 24 hours to about 2 months, from about 24 hours to about 1 month, from about 24 hours to about 3 weeks, from about 24 hours to about 14 days, from about 24 hours to about 7 days, from about 24 hours to about 3 days, from about 3 days to about 2 months, from about 3 days to about 1 month, from about 3 days to about 3 weeks, from about 3 days to about 14 days, from about 3 days to about 7 days, from about 7 days to about 2 months, from about 7 days to about 1 month, from about 7 days to about 3 weeks, from about 7 days to about 2 weeks, or greater than 2 months. In some embodiments, the repositioning force applied to at least one of the patient's teeth is present for about 24 hours, for about 3 days, for about 7 days, for about 14 days, for about 2 months, or for more than 2 months.

In some embodiments, the orthodontic appliances disclosed herein can provide on-track movement of at least one of the patient's teeth. On-track movement has been described further herein, e.g., at TABLE 1. In some embodiments, the orthodontic appliances disclosed herein can be used to achieve on-track movement of at least one of the patient's teeth to an intermediate tooth arrangement. In some embodiments, the orthodontic appliances disclosed herein can be used to achieve on-track movement of at least one of the patient's teeth to a final tooth arrangement.

In some embodiments, prior to moving, with the orthodontic appliance, at least one of the patient's teeth toward an intermediate arrangement or a final tooth arrangement, the orthodontic appliance has characteristics which are retained following the use of the orthodontic appliance. In some embodiments, prior to the moving step, the orthodontic appliance comprises a first flexural modulus. In certain embodiments, after the moving step, the orthodontic appliance comprises a second flexural modulus. In some embodiments, the second flexural modulus is at least 99%, at least 98%, at least 97%, at least 96%, at least 95%, at least 94%, at least 93%, at least 92%, at least 91%, at least 90%, at least 85%, at least 80%, at least 75%, at least 70%, at least 65%, at least 60%, at least 50%, or at least 40% of the first flexural modulus. In some embodiments, the second flexural modulus is greater than 50% of the first flexural modulus. In some embodiments, this comparison is performed following a period of time in which the appliance is applied. In some embodiments, the period of time is 3 days, 4 days, 5 days, 6 days, 7 days, 8 days, 9 days, 10 days, 11 days, 12 days, 13 days, 2 weeks, 3 weeks, 4 weeks, or greater than 4 weeks.

In some embodiments, prior to the moving step, the orthodontic appliance comprises a first elongation at break. In certain embodiments, after the moving step, the orthodontic appliance comprises a second elongation at break. In some embodiments, the second elongation at break is at least 99%, at least 98%, at least 97%, at least 96%, at least 95%, at least 94%, at least 93%, at least 92%, at least 91%, at least 90%, at least 85%, at least 80%, at least 75%, at least 70%, at least 65%, at least 60%, at least 50%, or at least 40% of the first elongation at break. In some embodiments, the second elongation at break is greater than 50% of the first elongation at break. In some embodiments, this comparison is performed following a period of time in which the appliance is applied. In some embodiments, the period of time is 3 days, 4 days, 5 days, 6 days, 7 days, 8 days, 9 days, 10 days, 11 days, 12 days, 13 days, 2 weeks, 3 weeks, 4 weeks, or greater than 4 weeks.

As provided herein, the methods disclosed can use the orthodontic appliances further disclosed herein. The orthodontic appliances can be directly fabricated using, e.g., the crystallizable resins disclosed herein. In certain embodiments, the direct fabrication comprises cross-linking the crystallizable resin.

The appliances formed from the crystallizable resins disclosed herein provide improved durability, strength, and flexibility, which in turn improve the rate of on-track progression in treatment plans. In some embodiments, greater than 60%, greater than 70%, greater than 80%, greater than 90%, or greater than 95% of patients treated with the orthodontic appliances disclosed herein (e.g., an aligner) are classified as on-track in a given treatment stage. In certain embodiments, greater than 60%, greater than 70%, greater than 80%, greater than 90%, or greater than 95% of patients treated with the orthodontic appliances disclosed herein (e.g., an aligner) have greater than 50%, greater than 55%, greater than 60%, greater than 65%, greater than 70%, greater than 75%, greater than 80%, greater than 85%, greater than 90%, or greater than 95% of their tooth movements classified as on-track.

As disclosed further herein, the cured polymeric material contains favorable characteristics that, at least in part, stem from the presence of polymeric crystals. These cured polymeric materials can have increased resilience to damage, can be tough, and can have decreased water uptake when compared to similar polymeric materials. The cured polymeric materials can be used for devices within the field of orthodontics, as well as outside the field of orthodontics. For example, the cured polymeric materials disclosed herein can be used to make devices for use in aerospace applications, automobile manufacturing, the manufacture of prototypes, and/or devices for use in durable parts production.

V. Experimental Methods

All chemicals were purchased from commercial sources and were used without further purification, unless otherwise stated.

$^1$H NMR and $^{13}$C NMR spectra were recorded on a BRUKER AC-E-200 FT-NMR spectrometer or a BRUKER Avance DRX-400 FT-NMR spectrometer. The chemical shifts are reported in ppm (s: singlet, d: doublet, t: triplet, q: quartet, m: multiplet). The solvents used were deuterated chloroform ($CDCl_3$, 99.5% deuteration) and deuterated DMSO ($d_6$-DMSO, 99.8% deuteration).

In some embodiments, the stress relaxation of a material or device can be measured by monitoring the time-dependant stress resulting from a steady strain. The extent of stress relaxation can also depend on the temperature, relative humidity and other applicable conditions (e.g., presence of water). In embodiments, the test conditions for stress relaxation are a temperature of 37±2° C. at 100% relative humidity or a temperature of 37±2° C. in water.

The dynamic viscosity of a fluid indicates its resistance to shearing flows. The SI unit for dynamic viscosity is the Poiseuille (Pa·s). Dynamic viscosity is commonly given in units of centipoise, where 1 centipoise (cP) is equivalent to 1 mPa·s. Kinematic viscosity is the ratio of the dynamic viscosity to the density of the fluid; the SI unit is $m^2/s$. Devices for measuring viscosity include viscometers and rheometers. For example, an MCR 301 rheometer from Anton Paar may be used for rheological measurement in rotation mode (PP-25, 50 s−1, 50-115° C., 3° C./min).

Determining the water content when fully saturated at use temperature can comprise exposing the polymeric material to 100% humidity at the use temperature (e.g., 40° C.) for a period of 24 hours, then determining water content by methods known in the art, such as by weight.

In some embodiments, the presence of a crystalline phase and an amorphous phase provide favorable material properties to the polymeric materials. Property values of the cured polymeric materials can be determined, for example, by using the following methods:
- stress relaxation properties can be assessed using an RSA-G2 instrument from TA Instruments, with a 3-point bending, according to ASTM D790; for example, stress relaxation can be measured at 30° C. and submerged in water, and reported as the remaining load after 24 hours, as either the percent (%) of initial load, and/or in MPa;
- storage modulus can be measured at 37° C. and is reported in MPa;
- $T_g$ of the cured polymeric material can be assessed using dynamic mechanical analysis (DMA) and is provided herein as the tan δ peak;
- tensile modulus, tensile strength, elongation at yield and elongation at break can be assessed according to ISO 527-2 5B; and tensile strength at yield, elongation at break, tensile strength, and Young's modulus can be assessed according to ASTM D1708.

Figure 5:
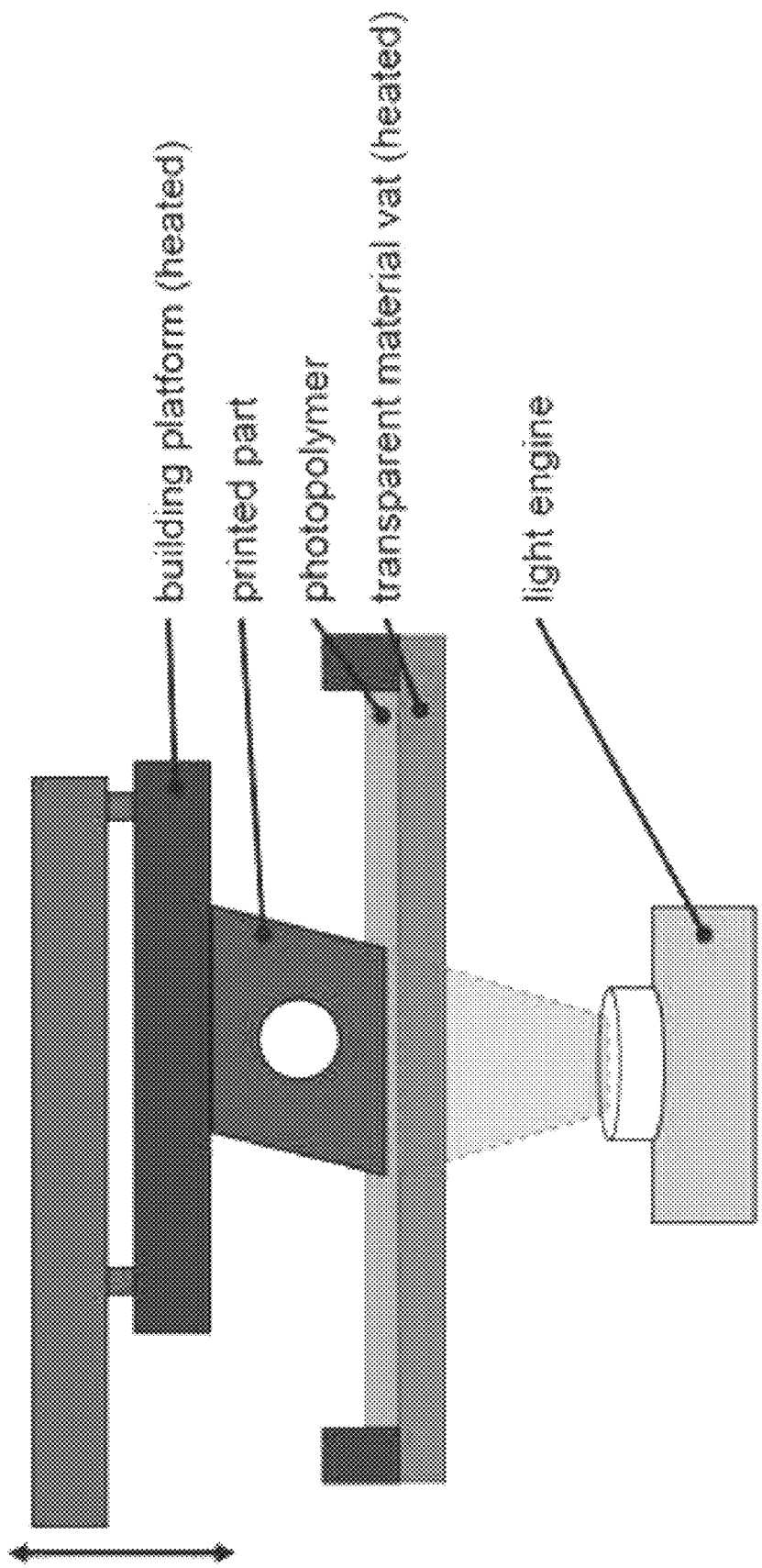
FIG. 5 shows a schematic configuration of a high temperature additive manufacturing device used for curing a curable compositions of the present disclosure by using a 3D printing process.

Additive manufacturing or 3D printing processes for generating a device herein (e.g., an orthodontic appliance) can be conducted using a Hot Lithography apparatus prototype from Cubicure (Vienna, Austria), which can substantially be configured as schematically shown in FIG. 5. In such cases, a photo-curable composition (e.g., resin) according to the present disclosure can be filled into the transparent material vat of the apparatus shown in FIG. 5, which vat can be heated to 90-110° C. The building platform can be heated to 90-110° C., too, and lowered to establish holohedral contact with the upper surface of the curable composition. By irradiating the composition with 375 nm UV radiation using a diode laser from Soliton, which can have an output power of 70 mW, which can be controlled to trace a predefined prototype design, and alternately raising the building platform, the composition can be cured layer by layer by a photopolymerization process according to the disclosure, resulting in a polymeric material according to present disclosure.

EXAMPLES

The following examples are given for the purpose of illustrating various embodiments of the invention and are not meant to limit the present disclosure in any fashion. The present examples, along with the methods described herein are presently representative of some embodiments, are exemplary, and are not intended as limitations on the scope of the invention. Changes therein and other uses which are encompassed within the spirit of the invention as defined by the scope of the claims will occur to those skilled in the art.

Example 1

Recovery of Guaiacol and Syringol from Polymeric Material

This example describes the recovery of the lignin derivatives Guaiacol and Syringol from polymeric material using base-mediated hydrolysis, which in various cases can be a medical device comprising such polymeric material, e.g., an orthodontic appliance. The base-mediated hydrolysis reaction is performed according to SCHEME 5:

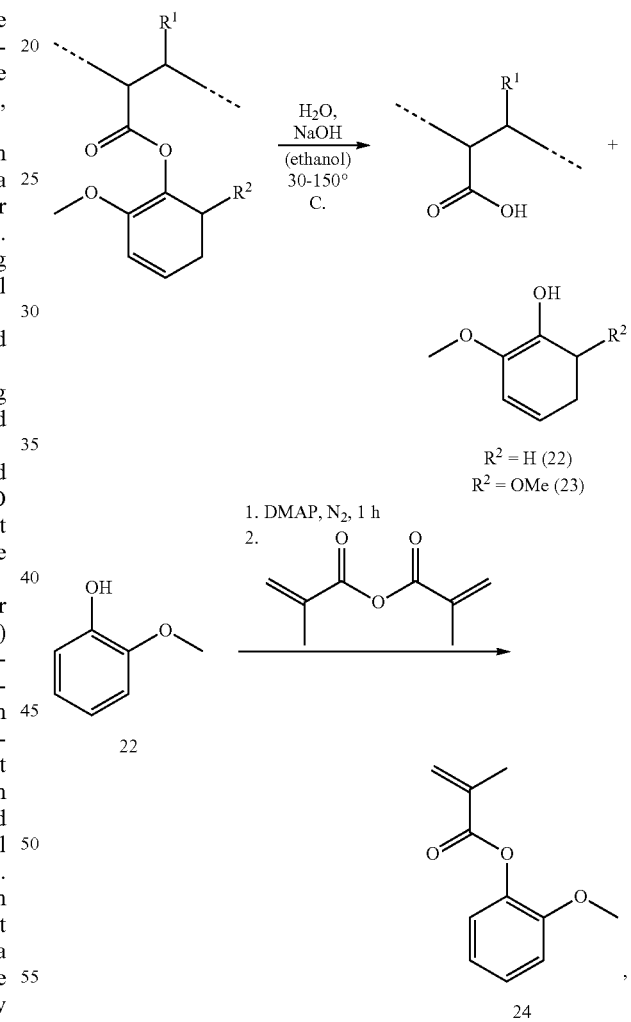

wherein $R^1$ is H (Guaiacol, 22) or methyl (Syringol, 23), and $R^2$ is H (poly-acrylate) or methoxyl (poly-methacrylate).

To that end, a polymeric material, e.g., a medical device or a portion thereof, comprising a poly-acrylate or poly-methacrylate backbone and Syringol and Guaiacol pendant groups coupled to the backbone, is placed into a solution comprising ethanol as solvent and 1 M sodium hydroxide. The reaction mixture is subsequently heated to a temperature between 30° C. and 150° C. and stirred for about 30 min to 5 hours. Optionally, the polymeric material can be pretreated prior to hydrolysis, e.g., broken down or milled into smaller portions to increase the surface area and, in some cases, improve the hydrolysis efficiency.

Following hydrolysis (which can be monitored using, e.g., chromatography), the resulting reaction mixture is cooled and subsequently distilled to generate a fraction comprising the crude Syringol and Guaiacol pendant groups. The crude pendant groups are subsequently further purified using a chromatography system comprising one or more column(s) (if >1, e.g., connected in series) comprising one or more ion exchange and/or normal and/or revered-phase resins. The Syringol and Guaiacol pendant groups are isolated in chemical purities of >95% and with a recovery yield of >50% based on the amounts of the respective pendant groups present in the initial polymeric material, and analyzed to confirm the chemical identity.

This example demonstrates that commercially important, as well as cost- and resource intensive building blocks can be recovered and prepared for recycling using the presently described methods.

Example 2

Synthesis of Guaiacol and Syringol Methacrylate from Recovered Pendant Groups

This example describes the recycling or reuse of the recovered pendant groups Syringol and Guaiacol as described in EXAMPLE 1 to synthesize the corresponding methacrylate derivatives as polymerizable building blocks (e.g., reactive diluents) for use in curable resins.

To that end, recovered Guaiacol (22, 1 equiv.) from EXAMPLE 1 and dimethylamino-pyridine (0.02 equiv.) are added to a round-bottom flask and sparged with $N_2$ for 1 h. The flask is cooled in an ice-water bath, and methacrylic anhydride (1.2 equiv.) is added to the mixture. The reaction is stirred at 45° C. overnight. Then, the cooled mixture is diluted with dichloromethane and washed with saturated sodium bicarbonate solution followed by 1 M NaOH solution. The organic layer is subsequently dried and concentrated, affording guaiacol methacrylate 24 in 29% yield and >95% chemical purity.

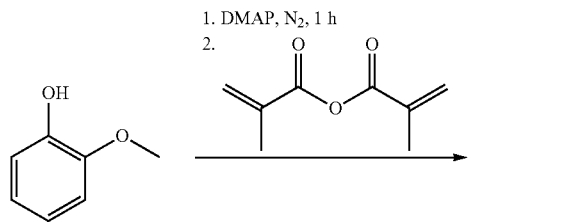

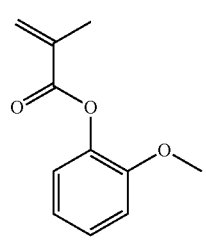

Recovered Syringol (23, 1 equiv.) from EXAMPLE 1 is dissolved in chloroform in a round-bottom flask. Lithium carbonate (1.1 equiv.) is added followed by methacrylic anhydride (1.1 equiv.). The reaction mixture is stirred at 50° C. or 60° C. overnight. Then, the solids are removed by filtration, and the filtrate is washed with saturated sodium bicarbonate solution and brine, dried over sodium sulfate, and concentrated. Column chromatography (eluting with 80% dichloromethane in hexanes) of the crude affords the product 25 in >95% yield and >95% chemical purity.

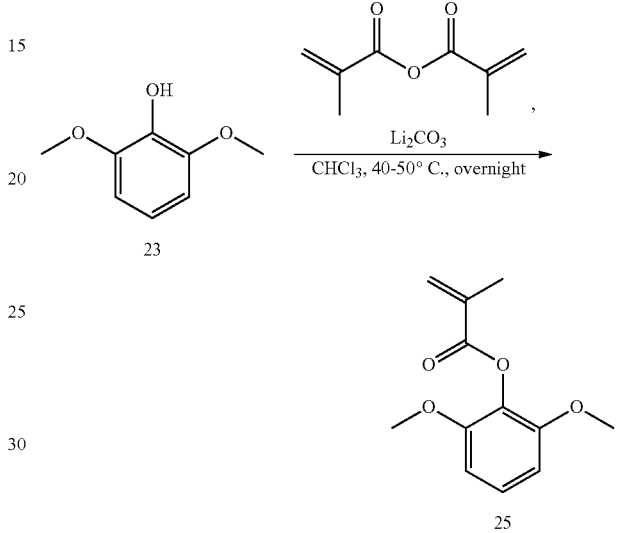

An alternative synthetic pathway involves the addition of 4-dimethyl-amino pyridine DMAP for >95% yield. In this process, Syringol (23, 1 equiv.), methacrylic anhydride (1.3 equiv.), triethylamine (1 equiv.), and butylated hydroxy toluene BHT (1 wt % total mass) —an equivalent amount of DMAP—is added equal to the amount of BHT added. The resulting mixture is dissolved in chloroform and reacted overnight at 60° C. The next day the solids are removed by filtration, and the filtrate washed with saturated sodium bicarbonate solution and brine, dried over sodium sulfate, and concentrated. Column chromatography with dichloromethane of the crude affords the product 25 in >95% yield and >95% chemical purity.

Example 3

Treatment Using an Orthodontic Appliance Comprising Recovered Material

This example describes the use of a directly 3D printed orthodontic appliance comprising polymeric material comprising recovered pendant groups, to move a patient's teeth according to a treatment plan. This example also describes the characteristics that the orthodontic appliance can have following its use, in contrast to its characteristics prior to use.

A patient in need of, or desirous of, a therapeutic treatment to rearrange at least one tooth has their teeth arrangement assessed. An orthodontic treatment plan is generated for the patient. The orthodontic treatment plan comprises a plurality of intermediate tooth arrangements for moving teeth along a treatment path, from the initial arrangement (e.g., that which was initially assessed) toward a final arrangement. The treatment plan includes the use of an orthodontic appliance, fabricated using photo-curable resins and methods disclosed further herein, to provide orthodontic appliances having low levels of hydrogen bonding units. In some embodiments, a plurality of orthodontic appliances is used, each of which can be fabricated using the photo-curable resins comprising one or more polymerizable monomers and methods disclosed further herein.

The orthodontic appliances are provided, and iteratively applied to the patient's teeth to move the teeth through each of the intermediate tooth arrangements toward the final arrangement. The patient's tooth movement is tracked. A comparison is made between the patient's actual teeth arrangement and the planned intermediate arrangement. Where the patient's teeth are determined to be tracking according to the treatment plan, but have not yet reached the final arrangement, the next set of appliances can be administered to the patient. The threshold difference values of a planned position of teeth to actual positions selected as indicating that a patient's teeth have progressed on-track are provided above in TABLE 1. If a patient's teeth have progressed at or within the threshold values, the progress is considered to be on-track. Favorably, the use of the appliances disclosed herein increases the probability of on-track tooth movement.

The assessment and determination of whether treatment is on-track can be conducted, for example, 1 week (7 days) following the initial application of an orthodontic appliance. Following this period of application, additional parameters relating to assessing the durability of the orthodontic appliance can also be conducted. For example, relative repositioning force (compared to that which was initially provided by the appliance), remaining flexural stress, relative flexural modulus, and relative elongation at break can be determined.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by some embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

What is claimed is:

1. A method of recovering a pendant group from a polymer, the method comprising:
providing the polymer comprising the following pendant group:

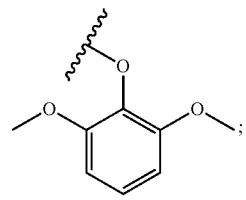

hydrolyzing a bond coupling the pendant group to the backbone of the polymer to produce a mixture; and
recovering the pendant group from the mixture.

2. A method of recovering a pendant group from a polymer, the method comprising:
providing the polymer comprising a synthetic polymer backbone;
cleaving a bond coupling the pendant group to the synthetic polymer backbone to produce a mixture; and
recovering the pendant group from the mixture; wherein the pendant group is

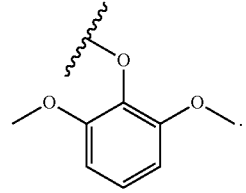

3. The method of claim 1, wherein the hydrolyzing comprises enzyme-mediated hydrolysis.
4. The method of claim 1, wherein the hydrolyzing comprises using a base at an elevated temperature.
5. The method of claim 4, wherein the elevated temperature is from 30° C. to 150° C.
6. The method of claim 4, wherein the base is an inorganic base.
7. The method of claim 6, wherein the inorganic base is an alkali metal hydroxide.
8. The method of claim 1, further comprising distilling the mixture to produce a crude pendant group.
9. The method of claim 8, wherein the distilling comprises steam-distillation.
10. The method of claim 8, further comprising purifying the crude pendant group using a chromatographic separation system to produce a fraction comprising the pendant group.
11. The method of claim 10, wherein the pendant group has a purity of at least 70%, 80%, 90%, or 95% w/w based on dry solids.
12. The method of claim 10, wherein the fraction comprises at most 5% w/w impurities based on dry solids.
13. The method of claim 12, wherein the impurities comprise decomposition products.
14. The method of claim 1, further comprising recovering at least 70%, 80%, 90%, or 95% of the pendant group relative to the amount of the pendant group present in the initial polymer.

15. The method of claim 1, wherein the polymer comprises, in a polymerized form, a monomer comprising the pendant group, and wherein the monomer is a compound of the following formula:

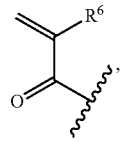

wherein ⁓ indicates a bond to the pendant group; and R$^6$ is H, halogen, or substituted or unsubstituted C$_{1-3}$ alkyl.

16. The method of claim 1, wherein the polymer comprises, in a polymerized form, a polyacrylate backbone.

17. The method of claim 16, wherein the polyacrylate backbone comprises, in a polymerized form, an acrylate moiety, a methacrylate moiety, or a combination thereof.

18. The method of claim 1, wherein the polymer is part of a polymeric material.

19. The method of claim 18, wherein the polymeric material is part of a device.

20. The method of claim 19, wherein the device is a medical device.

21. The method of claim 20, wherein the medical device is a dental appliance.

22. A process comprising:
providing a curable composition;
curing the curable composition to generate a polymer comprising a pendant group;
subjecting the polymer to reaction conditions to cleave a bond coupling the pendant group to the backbone of the polymer;
generating a mixture comprising the pendant group; and
recovering at least 70%, 80%, 90%, or 95% of the pendant group relative to the amount of the pendant group present in the polymer;
wherein the recovered pendant group is

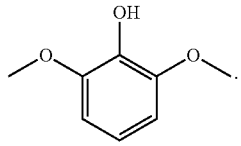

23. The process of claim 22, further comprising synthesizing a polymerizable monomer using the recovered pendant group.

24. The process of claim 23, wherein the polymerizable monomer is a compound according to the following formula:

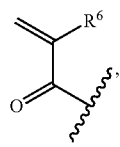

wherein ⁓ indicates a bond to the recovered pendant group and
R$^6$ is H, halogen, methoxy, or substituted or unsubstituted C$_{1-3}$ alkyl.

25. The process of claim 24, wherein R$^6$ is H or methoxy.

26. The process of claim 24, wherein the polymerizable monomer is used as a component of the curable composition.

27. The method of claim 21, wherein the dental appliance is an orthodontic appliance.

* * * * *